(12) United States Patent
Sly et al.

(10) Patent No.: US 11,177,960 B2
(45) Date of Patent: Nov. 16, 2021

(54) SYSTEMS AND METHODS TO VERIFY IDENTITY OF AN AUTHENTICATED USER USING A DIGITAL HEALTH PASSPORT

(71) Applicant: Sharecare AI, Inc., Palo Alto, CA (US)

(72) Inventors: Axel Sly, Palo Alto, CA (US); Srivatsa Akshay Sharma, Santa Clara, CA (US); Brett Robert Redinger, Oakland, CA (US); Devin Daniel Reich, Olympia, WA (US); Geert Trooskens, Meise (BE); Meelis Lootus, London (GB); Young Jin Lee, Vancouver (CA); Ricardo Lopez Arredondo, Schertz, TX (US); Frederick Franklin Kautz, IV, Fremont, CA (US); Satish Srinivasan Bhat, Fremont, CA (US); Scott Michael Kirk, Belmont, CA (US); Walter Adolf De Brouwer, Los Altos Hills, CA (US); Kartik Thakore, Santa Clara, CA (US)

(73) Assignee: Sharecare AI, Inc., Palo Alto, CA (US)

( * ) Notice: Subject to any disclaimer, the term of this patent is extended or adjusted under 35 U.S.C. 154(b) by 0 days.

(21) Appl. No.: 17/235,889

(22) Filed: Apr. 20, 2021

(65) Prior Publication Data

US 2021/0328801 A1 Oct. 21, 2021

Related U.S. Application Data

(60) Provisional application No. 63/013,536, filed on Apr. 21, 2020.

(51) Int. Cl.
*H04L 9/32* (2006.01)
*H04L 9/08* (2006.01)
(Continued)

(52) U.S. Cl.
CPC .......... *H04L 9/3231* (2013.01); *G06K 7/1417* (2013.01); *G06N 5/04* (2013.01);
(Continued)

(58) Field of Classification Search
CPC ..... H04L 9/3231; H04L 9/0841; H04L 9/085; H04L 9/0894; H04L 9/3228;
(Continued)

(56) References Cited

U.S. PATENT DOCUMENTS

| | | |
|---|---|---|
| 8,275,175 B2 | 9/2012 | Baltatu et al. |
| 8,543,428 B1 | 9/2013 | Jones, III et al. |

(Continued)

OTHER PUBLICATIONS

Parkhi, Omkar M., et. al., "Deep Face Recognition", 2015, 12 pages.

(Continued)

*Primary Examiner* — Techane Gergiso
(74) *Attorney, Agent, or Firm* — Haynes Beffel & Wolfeld LLP; Sikander M. Khan

(57) ABSTRACT

The technology disclosed relates to authenticating users using a plurality of non-deterministic registration biometric inputs. During registration, a plurality of non-deterministic biometric inputs are given as input to a trained machine learning model to generate sets of feature vectors. The non-deterministic biometric inputs can include a plurality of face images and a plurality of voice samples of a user. A characteristic identity vector for the user can be determined by averaging feature vectors. During authentication, a plurality of non-deterministic biometric inputs are given as input to a trained machine learning model to generate a set of authentication feature vectors. The sets of feature vectors are projected onto a surface of a hyper-sphere. The system can authenticate the user when a cosine distance between the (Continued)

authentication feature vector and a characteristic identity vector for the user is less than a pre-determined threshold.

18 Claims, 23 Drawing Sheets

(51) Int. Cl.
  *G06N 20/00* (2019.01)
  *G06K 7/14* (2006.01)
  *G06N 5/04* (2006.01)
(52) U.S. Cl.
  CPC .............. *G06N 20/00* (2019.01); *H04L 9/085* (2013.01); *H04L 9/0841* (2013.01); *H04L 9/0894* (2013.01); *H04L 9/3228* (2013.01); *H04L 9/3239* (2013.01); *H04L 9/3247* (2013.01); *H04L 9/3297* (2013.01)
(58) Field of Classification Search
  CPC ... H04L 9/3239; H04L 9/3247; H04L 9/3297; H04L 9/3249; H04L 9/3252; H04L 9/3255; H04L 9/3257; H04L 63/0861; H04L 63/0838; H04L 9/0863; H04L 9/0869; H04L 9/0872; H04L 9/0844; H04L 9/0847; G06N 20/00; G06N 5/04; G06K 7/1417; G06K 9/00221; G06K 9/00228; G06K 9/00234; G06K 9/00241; G06K 9/00248; G06K 9/00255; G06K 9/00261; G06K 9/00281; G06K 9/00295; G06K 9/00288; G06K 9/00275; G06K 9/00268; G06K 9/00308; G06K 9/00315; G06K 9/00302; G06K 2009/00322; G06K 2009/00328; G06K 9/0061; G06K 9/00617; G06K 9/00677; G06K 9/00892; H04W 12/02; G06Q 20/3276; G06Q 20/3274; G06F 21/6245; G06F 21/6254; G06F 21/6263; G06F 21/6272; G06F 21/6281; G06F 21/32
  See application file for complete search history.

(56) References Cited

U.S. PATENT DOCUMENTS

| | | | |
|---|---|---|---|
| 9,839,376 B1 | 12/2017 | Ross et al. | |
| 11,042,719 B2* | 6/2021 | Rodriguez | G06Q 20/3672 |
| 2006/0206724 A1 | 9/2006 | Schaufele et al. | |
| 2011/0172499 A1 | 7/2011 | Simons-Nikolova et al. | |
| 2011/0291834 A1 | 12/2011 | Boldyrev et al. | |
| 2012/0162404 A1 | 6/2012 | Howell et al. | |
| 2013/0046761 A1 | 2/2013 | Soderberg et al. | |
| 2013/0266195 A1 | 10/2013 | Shiell et al. | |
| 2015/0213207 A1 | 7/2015 | Amarasingham et al. | |
| 2015/0324686 A1 | 11/2015 | Julian et al. | |
| 2015/0339523 A1 | 11/2015 | Tsunematsu | |
| 2015/0363709 A1 | 12/2015 | Kamei et al. | |
| 2016/0253549 A1 | 9/2016 | Ramic | |
| 2017/0206691 A1 | 7/2017 | Harrises et al. | |
| 2018/0165781 A1* | 6/2018 | Rodriguez | G06Q 40/00 |
| 2018/0176017 A1* | 6/2018 | Rodriguez | H04L 63/0861 |
| 2018/0289334 A1 | 10/2018 | De Brouwer et al. | |
| 2018/0329893 A1* | 11/2018 | Hill | G06F 21/629 |
| 2019/0082211 A1 | 3/2019 | Vats | |
| 2020/0195436 A1* | 6/2020 | Khan | G06F 21/45 |
| 2020/0302088 A1* | 9/2020 | Lee | H04L 63/0807 |
| 2021/0027869 A1* | 1/2021 | Sayani | G16H 30/20 |

OTHER PUBLICATIONS

Parkhi, Omkar M., et. al., Visual Geometry Group, 4 pages, [Retrived on Apr. 18, 2021], Retrieved from the Internet < URL: https://www.robots.ox.ac.uk/~vgg/software/vgg_face/>.
Deng, Jiankang, et. al., "ArcFace: Additive Angular Margin Loss for Deep Face Recognition", Feb. 9, 2019, 11 pages.
Wikipedia, "Diffie-Hellman key exchange", 12 pages [Retrieved on Apr. 18, 2021], Retrieved from the Internet < URL: https://en.wikipedia.org/wiki/Diffie-Hellman_key_exchange>.
WhatIs.com, "What is Diffie-Hellman Key Exchange?", Mar. 2019, 5 pages, [Retrieved on Apr. 18, 2021], Retrieved from the Internet < URL: https://searchsecurity.techtarget.com/definition/Diffie-Hellman-key-exchange>.
Kallam, Sivanagaswathi, "Duffie-Hellman:Key Exchange and Public Key Cryptosystems", Sep. 30, 2015, 27 pages.
Xie, Renjie et al., "A Deep Information-theoretic Framework for Robust Biometric Recognition", Feb. 23, 2019, 7 pages.
U.S. Appl. No. 17/235,871—Office Action dated Jun. 24, 2021, 8 pages.
U.S. Appl. No. 15/946,629—Office Action dated May 20, 2020, 10 pages.
Kocabey, Enes, et. al., "Face to BMI Using Computer Vision to Infer Body Mass Index on Social Media", 2017, 4 pages.
U.S. Appl. No. 15/946,629—Response to Office Action dated May 20, 2020, filed Aug. 20, 2020, 13 pages.
U.S. Appl. No. 15/946,629—Office Action dated Oct. 23, 2020, 9 pages.
U.S. Appl. No. 15/946,629—Notice of Allowance dated Jan. 22, 2021, 16 pages.
U.S. Appl. No. 16/802,485—Notice of Allowance dated Feb. 18, 2021, 10 pages.
Wen, Lingyun, et. al., "A computational approach to body mass index prediction from face images", Feb. 9, 2013, 9 pages.
"Diffie-Hellman Key Exchange", 1 page, [Retrieved on Mar. 18, 2021], Retrieved from the Internet < URL: https://i.stack.imgur.com/AEx0X.png>.

* cited by examiner

Diffie-Hellman Key Exchange

Worker's Device 194 and Registration Server 111 have the following:

$p = 23$ (a prime number)    $g = 11$ (a generator)

Worker's Device 194

Worker's Device chooses a secret random number $a = 6$

552
Worker's Device computes:
$A = g^a \bmod p$
$A = 11^6 \bmod 23 = 9$

Worker's Device Receives $B = 5$ From Registration Server

572
Secret Key $= K = B^a \bmod p$
$K = 5^6 \bmod 23 = 8$

Registration Server 111

Registration Server chooses a secret random number $b = 5$

558
Registration Server's computes:
$B = g^b \bmod p$
$B = 11^5 \bmod 23 = 5$

Registration Server Receives $A = 9$ From Worker's Device

582
Secret Key $= K = A^b \bmod p$
$K = 9^5 \bmod 23 = 8$

Step 1, Step 2, Step 3, Step 4

Shared Secret is 8

FIG. 5A

SYSTEMS AND METHODS TO VERIFY IDENTITY OF AN AUTHENTICATED USER USING A DIGITAL HEALTH PASSPORT

PRIORITY APPLICATION

This application claims the benefit of U.S. Patent Application No. 63/013,536, entitled "ARTIFICIAL INTELLIGENCE-BASED GENERATION OF ANTHROPOMORPHIC SIGNATURES AND USE THEREOF," filed Apr. 21, 2020. The provisional application is incorporated by reference for all purposes.

INCORPORATIONS

The following materials are incorporated by reference as if fully set forth herein:

U.S. Provisional Patent Application No. 62/734,840, titled, "HASH-BASED EFFICIENT COMPARISON OF SEQUENCING RESULTS," filed Sep. 21, 2018;

U.S. Provisional Patent Application No. 62/734,872, titled, "BIN-SPECIFIC AND HASH-BASED EFFICIENT COMPARISON OF SEQUENCING RESULTS," filed Sep. 21, 2018;

U.S. Provisional Patent Application No. 62/734,895, titled, "ORDINAL POSITION-SPECIFIC AND HASH-BASED EFFICIENT COMPARISON OF SEQUENCING RESULTS," filed Sep. 21, 2018;

U.S. Provisional patent application Ser. No. 16/816,153 titled, "SYSTEM AND METHOD WITH FEDERATED LEARNING MODEL FOR MEDICAL RESEARCH APPLICATIONS," filed Mar. 11, 2020;

US Nonprovisional Patent Application No. 62/816,880 titled, "SYSTEM AND METHOD WITH FEDERATED LEARNING MODEL FOR MEDICAL RESEARCH APPLICATIONS," filed Mar. 11, 2019;

U.S. Provisional Patent Application No. 62/942,644 titled, "SYSTEMS AND METHODS OF TRAINING PROCESSING ENGINES," filed Dec. 2, 2019;

US Provisional Patent Application Nos. 62/883,070 titled, "ACCELERATED PROCESSING OF GENOMIC DATA AND STREAMLINED VISUALIZATION OF GENOMIC INSIGHTS," filed Aug. 5, 2019;

U.S. Provisional Patent Application No. 62/942,644, titled, "SYSTEMS AND METHODS OF TRAINING PROCESSING ENGINES," filed Dec. 2, 2019;

U.S. Provisional Patent Application No. 62/975,177, filed Feb. 11, 2020, titled, "ARTIFICIAL INTELLIGENCE-BASED DRUG ADHERENCE MANAGEMENT AND PHARMACOVIGILANCE";

U.S. Provisional Patent Application No. 62/810,549, titled, "SYSTEM AND METHOD FOR REMOTE MEDICAL INFORMATION EXCHANGE," filed Feb. 26, 2019;

U.S. patent application Ser. No. 15/946,629, entitled "IMAGE-BASED SYSTEM AND METHOD FOR PREDICTING PHYSIOLOGICAL PARAMETERS," filed on Apr. 5, 2018;

U.S. Provisional Application No. 62/481,691, entitled "METHOD OF BODY MASS INDEX PREDICTION BASED ON SELFIE IMAGES," filed on Apr. 5, 2017;

U.S. Provisional Patent Application No. 62/883,639, titled "FEDERATED CLOUD LEARNING SYSTEM AND METHOD," filed on Aug. 6, 2019;

U.S. Provisional Patent Application No. 62/816,880, titled "SYSTEM AND METHOD WITH FEDERATED LEARNING MODEL FOR MEDICAL RESEARCH APPLICATIONS," filed on Mar. 11, 2019;

U.S. Provisional Patent Application No. 62/671,823, titled "SYSTEM AND METHOD FOR MEDICAL INFORMATION EXCHANGE ENABLED BY CRYPTO ASSET," filed on May 15, 2018; and U.S. Nonprovisional patent application Ser. No. 16/167,338, titled "SYSTEM AND METHOD FOR DISTRIBUTED RETRIEVAL OF PROFILE DATA AND RULE-BASED DISTRIBUTION ON A NETWORK TO MODELING NODES," filed on Oct. 22, 2018.

FIELD OF THE TECHNOLOGY DISCLOSED

The technology disclosed is related to application of machine learning techniques and use of non-deterministic biometric data to establish and use authentication credentials.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

In a post-COVID work environment, employers want to ensure that workers coming back to work are healthy. A worker can provide her health status and/or laboratory test results indicating that she is not infected with the virus. Authenticating that a valid worker is presenting this information presents many challenges. A central database storing workers' health and identification information may not be maintained due to privacy issues. The employer validating the worker's request needs to ensure that the client device is not presenting another user from the requesting worker's device and using worker's credentials to get access to the workplace. A validator may also be malicious and trying to log valid credentials to allow another user to bypass the system at a later time.

Accordingly, an opportunity arises to develop systems and methods to address the challenges of safely opening the places of work to workers without compromising the health and identification data of workers.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 5A presents a high-level overview of an encryption technique with forward secrecy that can be used to generate a shared key for communication between worker's device and registration server.

DETAILED DESCRIPTION

Figure 1:
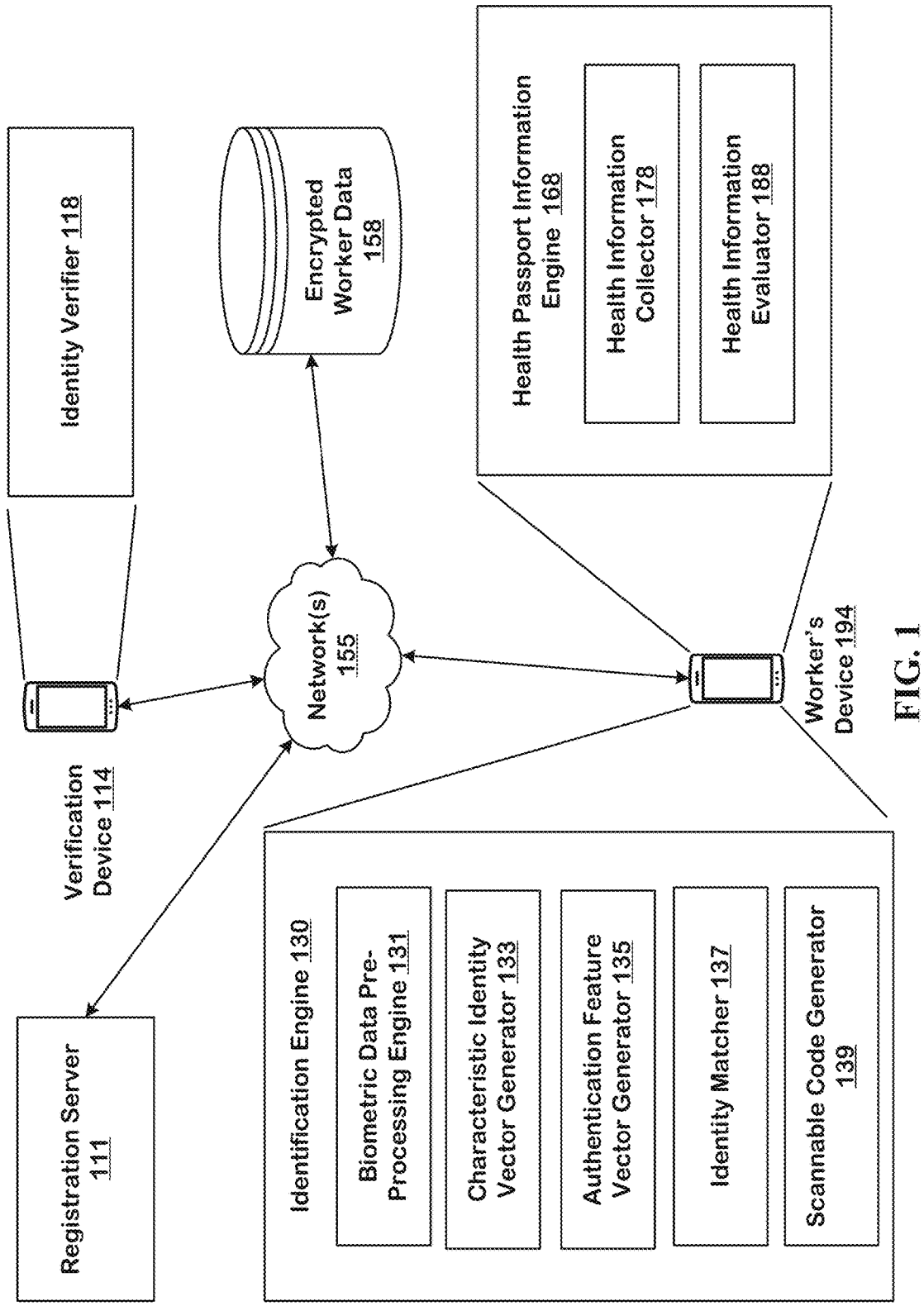
FIG. 1 shows an architectural level schematic of a system that can establish authentication credentials using non-deterministic biometric inputs, use these credentials to authenticate users and verify that a request is being sent by an authenticated user.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

A health passport is desirable as workers return to offices, factories and other places of employment in a post-COVID-19 world. This is difficult to do without a national identity database, on a decentralized basis. At the same time, a secure passport is desirable, as the opportunity to return to workplaces creates incentives for workers, employment agencies and employers to borrow credentials of an eligible worker and reuse them for multiple workers.

The technology disclosed secures identities, authentication credentials and health information, without needing to rely on a central database to store personally identifiable or health information. At registration, user credentials can be established based on reliable and even verifiable information. A cryptographic signature can be applied to locally retained data and the registration server can retain the signature but not need to retain the information signed or even to retain any personally identifiable information. Unique IDs and keys, used to generate cryptographic signatures of identity documentation locally retained on a mobile device, can be combined with locally encoded biometric observations to securely authenticate users. Locally retaining identity documentation avoids the privacy risk associated with a national database. Health data entry can be verified locally and retained. Upon request, a scannable code can be generated on a mobile device, in response to a worker making an authenticated request, including the worker providing biometric input such as voice and face image samples, used to generate the authentication credentials. The code can be presented with a name and image of the identified person. By embedding a time stamp and optionally embedding location information in the scannable code, replay can be detected and rejected.

Non-deterministic biometric input, such as voice and face images, can be used to generate a characteristic identity vector, against which authentication input is measured. Biometric input is variable in the sense that a voice sounds somewhat different from day to day and a face is at a different angle, with different hair appearance, or in different light from photo to photo. Multiple biometric samples are collected to represent a range of sounds and appearances. There are a variety of ways to generate features of and to average these samples, in order to create a representative biometric identity indicator. In one example, a convolutional neural network (CNN) is applied to samples to extract features from each sample, after some number of layers. For instance, an ImageNet CNN or ArcFace model (available at www.arxiv.org/abs/1801.07698) can be applied to extract image features. These features can be used to embed an image into a multi-dimensional space and normalized to position the image on a surface, one unit from the center of the multi-dimensional space. Then, an average of multiple samples on the surface can be selected to represent the user.

A distance can be used to compare an authentication feature vector with a characteristic identity vector. When vectors are projected onto a unit hyper-sphere, a cosine distance can be used to compare the authentication and identity vectors. Alternatively, a Euclidean or other distance measure can be used. This is the nature of embedding spaces. Yet alternatively, a distance preserving hash can be applied to a feature set and distances can be approximated by differences between resulting hashes. Distances that are small enough, vectors that are close enough together, are considered to match and authentication is confirmed.

The technology disclosed can also apply a binning function to non-integer values of feature vectors during registration. The binning function quantizes the values of elements of the feature vectors. The same binning function can then be applied to an authentication feature vector. The ranges of values that map to the same bins are selected to accommodate variations in facial images and voice samples of a user. Therefore, after applying the binning function, the quantized feature vectors have similar values for corresponding elements of authentication feature vectors. One or more facial images of a user can be processed by trained machine learning models to generate respective registration feature vectors. Similarly, during authentication, one or more facial images of a user can be processed by trained machine learning models to generate respective authentication feature vectors. Hashes of quantized registration feature vectors are matched to hashes of quantized authentication feature vectors to authenticate a user.

Health passport information is stored on the mobile device and evaluated by a trustworthy application. This can be done for tests, vaccinations, answers to screening questions, exposure to virus data, and the like. For answers to screening questions, the trustworthy application can administer a questionnaire. The app on the mobile device can process answers to questions and laboratory or test results to determine that the user is ready to return to work. The system can also include secure APIs to access a user's test results or laboratory results from laboratories, clinics or hospitals.

A trustworthy application running on the mobile device can generate a scannable code and additional verification information. The app authenticates the user, then evaluates locally stored health information to determine the user's health status. The app generates a scannable code that represents the results of evaluating the health information. A time stamp, a nonce code and, optionally location information, can be embedded in the scannable code to make replay detectable.

A verification device scans and can accepts the code. An identification photograph can be displayed by the app with the scannable code so that a verification operator can positively match the person presenting the code to the photo. Alternatively, the verification device can compare a live photograph of the person presenting the code to the identification photo. Yet alternatively, the scan code can convey an identification code with which the verification device can retrieve a stored photograph, name and other identification information, stored with the verification device without the need for a central database. The photo can be used by an operator or for comparison to a live photo of the person presenting the scan code.

Optionally, the stored health information can be exposed by the health passport app, with the user's authorization, for inspection by an authority who has a need to verify the information relied on to generate the scannable code.

The mechanisms for registration, authentication, verification of health information, evaluation of health information to generate a scannable code, and scanning to verify a health passport are aspects of the technology disclosed. In combination, these technologies allow a user to possess a trustworthy passport with a verified identity and trusted health information. Risks of presentation by the wrong person or replay are minimized. When the verification device accesses a remote server to verify signatures, even the risk of tampering with the verification device is minimized.

Environment

We describe a system for registering, authenticating, and verifying health status of a user to provide a health passport to the user. The system is described with reference to FIG. 1 showing an architectural-level schematic of a system in accordance with an implementation. Because FIG. 1 is an architectural diagram, certain details are intentionally omitted to improve the clarity of the description. The discussion of FIG. 1 is organized as follows. First, the elements of the figure are described, followed by their interconnection. Then, the use of the elements in the system is described in greater detail.

FIG. 1 includes a system 100. This paragraph names labeled parts of system 100. The figure illustrates a registration server 111, a verification device 114, an identity verifier 118, a worker's (or user's) device 194, an identification engine 130, a health passport information engine 168, an encrypted worker database 158, and a network(s) 155. The identification engine 130 further includes a biometric data pre-processing engine 131, a characteristic identity vector generator 133, an authentication feature vector generator 135, an identity matcher 137, and a scannable code generator 139. The health passport information engine 168 further includes a health information collector 178, and a health information evaluator 188. The identification engine 130 and the health passport information engine 168 can be deployed on the worker's device 194. The identity verifier 118 can be deployed on the verification device 114. The network(s) 155 couples the registration server 111, the verification device 114, the encrypted worker database 158, and the worker's device 194.

Figure 2A:
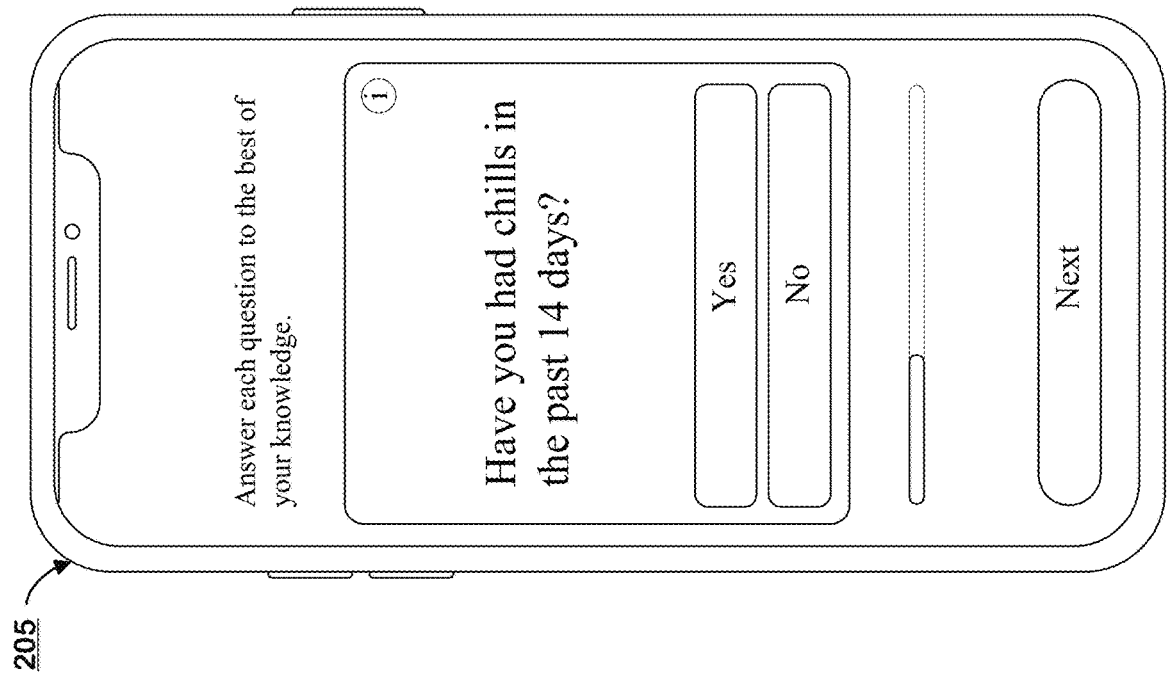
FIGS. 2A and 2B present examples of a user interface of a trustworthy app on a worker's device for sending a request to a validator and receiving approval to return to work.
Figure 2A:
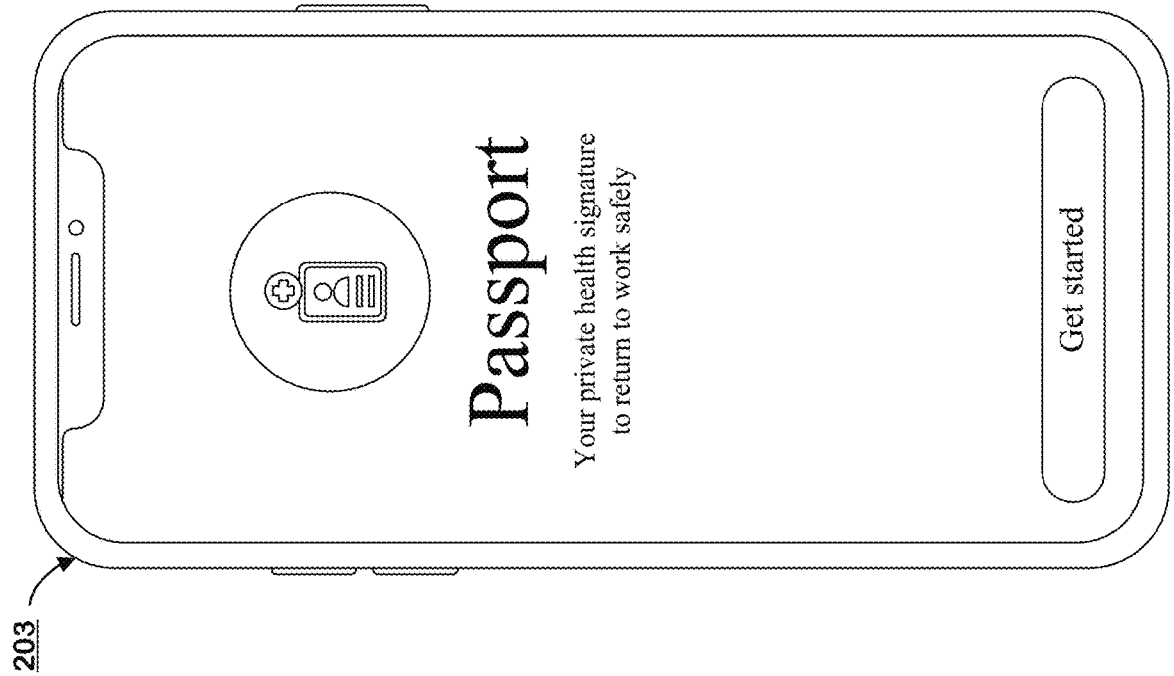
Figure 2B:
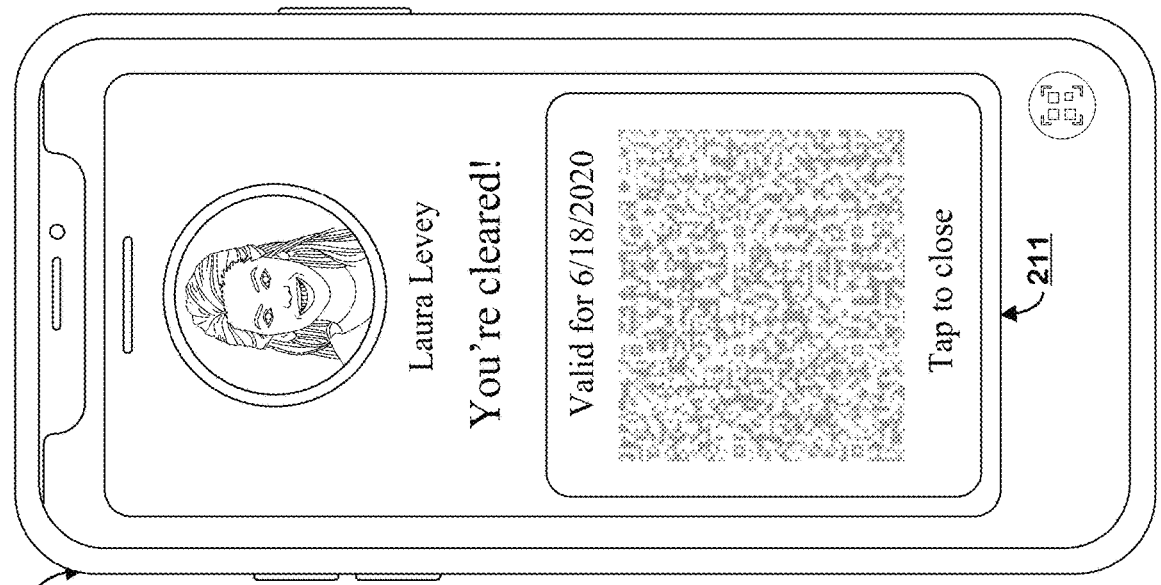
Figure 2B:
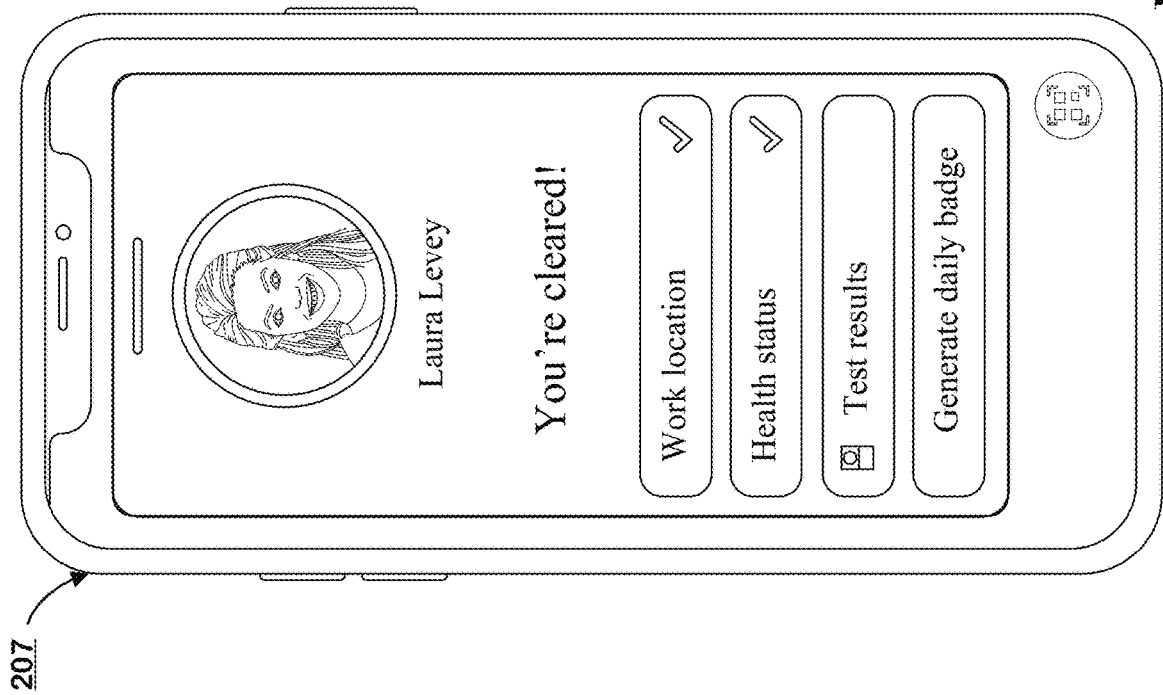

The technology disclosed enables workers (or users) to provide their health information to the health passport information engine 168 so that they can get a health passport to return to their place of work. The health information collector 178 can include logic to collect relevant health information from the worker. FIGS. 2A and 2B present examples of a user interface of trustworthy application running on the worker's device that can be used to collect health information from workers. The worker can click the "Get Started" button on the interface 203 in FIG. 2A to provide their health information. The app can then ask a series of questions to collect health information from the user. An example question is presented on a user interface 205, "Have you had chills in the past 14 days?" The worker can answer the question by selecting an option "yes" or "no" (206).

The app can also prompt the user to provide laboratory test results and/or vaccination records. The user can take a picture of their laboratory test results or vaccination cards and upload the image to the app. The app can use a variety of techniques to extract test and vaccination data from uploaded images of test results or vaccination cards. For example, the app can use optical character recognition (or OCR) to extract information from images of laboratory test results of vaccination records. OCR can convert text in images into raw text that can be edited by the system or provided as input to other models for further processing. OCR can be applied to text written by hand, machine printed text or text in portable document format (PDF) files or image files. The system can apply OCR on vaccine records that are either electronic records or printed cards to extract the vaccination information. In one implementation, the system can send, with user's approval, the vaccination information to an employer or other organizations. The system can also use a trained machine learning model to extract vaccination information or other data from images uploaded by the user.

The app can verify test results of vaccination records by accessing third parties such as hospitals, clinics, pharmacies or vaccine providers using application programming interface (or APIs). The app can access electronic medical records (EMRs) that are maintained by hospitals or electronic health records (EHRs) that are maintained by other organizations using the APIs to get vaccination record of a user or verify vaccination record or other test results. For example, a vaccine provider or vaccine manufacturer may maintain a database of users who have received vaccination. The app can access the vaccine provider's portal or database using an API to verify a user's vaccination record.

The app can also connect to other health and fitness apps or systems using third party APIs such as HealthKit™ API or Human™ API to collect health related information about the user. The technology disclosed, with user's approval, may access these health and fitness apps to collect user's health related data. In some cases, the health and fitness apps may connect to the third parties such as hospitals, pharmacies or vaccine providers to collect the required data on behalf of the trustworthy app. For example, Human™ API provides APIs for accessing health data from several health data sources such as hospitals, clinics, pharmacies, laboratories, etc. The trustworthy app can access user's vaccination record or test results using these APIs and verify that the user is healthy and vaccinated to return to place of work. The app can verify the test results and vaccination records before generating a scan code for the authenticated user. The test results and vaccination record of the user may not be sent to registration server or employer for privacy reasons. In some cases, the app may send selected test results or vaccination records of users to employers or other organizations with approval from the user.

At the end of the survey, the app can process the answers from the worker and generate a result as shown on the user interface 207. The worker's picture and name can be displayed on the user interface. The system processes the health and identity information locally so that no personal identification information or sensitive health data leaves the worker's device. In one example, the system can be used to allow workers to come back to their places of work in a post-COVID world.

A health information evaluator 188 can evaluate the data collected by the health information collector to determine whether the worker can be allowed back to the workplace. The system can request additional information such as laboratory test results, etc. Suppose a worker has been sick and needs to return to work. The worker is now feeling better and is symptom-free. He has taken SARS-CoV-2 serology and molecular tests. The test results report that he was positive in the serology test indicating that he was infected with the virus and has developed an immune response to it. He is negative for the molecular RT-PCR test indicating that he is clear of the virus and he is likely fit to return to work. The worker can upload his test results either by manually inputting the results or by scanning or taking pictures of laboratory test reports and uploading the images to the app running on his device. This process can be used for providing tests, vaccinations, answers to screening questions, exposure-to-virus data, and the like. For answers to screening questions, the health information collector 178 component of the application on the worker's mobile device can administer a questionnaire as described above. The health information evaluator 188 on the worker's device can process answers to questions and laboratory or test results to determine if the worker is healthy to return to work.

The problem of verifying the health status of an employee for the purpose of allowing them to return to work poses many challenges. For example, a worker's device may present a user who may be using another worker's credentials to get approval to return to work. A validator may also be malicious and trying to log valid credentials to allow another user to bypass the system at a later time. The technology disclosed includes logic to ensure that the return-to-work request is sent by an authenticated user and avoid replays or logging of credentials. To address this challenge, the worker's device generates a scannable code which may be valid for a limited amount of time and sends that to the verification device 114. The scannable code includes data that can be used by the verification device to ensure that the request to return to work is received from an authenticated worker. An example scannable code 211 is illustrated on a user interface 209 in FIG. 2B. The scannable code can be generated in response to a worker clicking on the button "Generate daily badge" as shown on the user interface 207 in FIG. 2B. The worker's image and name can be displayed on the user interface of the device along with the scannable code 211. The technology disclosed includes secure identities and authentication credentials to ensure that the request to return to work is sent by an authenticated worker. The system can embed timestamps and one-time nonce code in the scannable code so that replays can be detected and rejected.

The technology disclosed can use non-deterministic biometric inputs to authenticate workers. The identification engine 130 can process non-deterministic inputs such as face images and voice samples to authenticate users. These biometric inputs are non-deterministic because each face image and voice sample from the user can be different. For example, the face image can be at different angles, with different hair appearance or in different light from photo to photo. Similarly, the voice of the user can sound different from day to day.

During the registration process, the characteristic identity vector generator 133 can process a range of facial images and sound samples obtained from the worker to generate a characteristic identity vector, against which the worker can be authenticated. Trained machine learning models such as convolutional neural networks (CNNs) can be applied to a plurality of pre-processed biometric inputs such as face images and voice samples to generate a plurality of feature vectors for respective face images and voice samples. Feature vectors for face images and voice samples can be stacked to generate a plurality of registration embeddings or registration feature vectors for a worker. The characteristic identity vector generator 133 can apply a variety of techniques to average these feature vectors to create a representative biometric identity indicator. For example, in one instance features can be used to embed an image into a multi-dimensional space and normalized to position the image on the surface of a unit hyper-sphere. An average of multiple samples for a user on the surface of the unit hyper-sphere can be selected to represent the user.

The system can authenticate the worker during login by generating an authentication feature vector using non-deterministic biometric inputs from the user. The authentication feature vector generator 135 can generate an authentication feature vector using trained machine learning models as used during the registration process described above. The authentication feature vector is then matched to the characteristic identity vector by the identity matcher 137. A distance can be used to compare an authentication feature vector with the characteristic identity vector. When vectors are projected onto a unit hyper-sphere, a cosine distance can be used to compare the authentication and identity vectors. Other distance measures such as Euclidean distance can be used to match the authentication vector to the identity vector. A distance-preserving hash can be applied to a feature set and distances can be approximated by differences between resulting hashes. Distances that are small enough, vectors that are close enough together, are considered to match and authentication is confirmed.

The scannable code generator 139 can generate a scannable code 211 after the identification engine 130 has authenticated the user. The scannable code can be scanned by the verification device 114. The verification devices 114 can include an identity verifier 118 that can communicate with the registration server 111 to verify that a return-to-work request is received from an authenticated user. An identification photograph can be displayed by the app with the scannable code so that a verification operator can positively match the person presenting the code to the photo. Alternatively, the verification device can compare a live photograph of the person presenting the code to the identification photo. Yet alternatively, the scan code can convey an identification code with which the verification device can retrieve a stored photograph, name and other identification information, stored with the verification device without the need for a central database. The photo can be used by an operator or for comparison to a live photo of the person presenting the scan code. The system can store the worker's identification data such as a photograph, name or other identification information in the encrypted worker database 158. The identification information is encrypted at rest when stored in the database 158.

Completing the description of FIG. 1, the components of the system 100, described above, are all coupled in communication with the network(s) 155. The actual communication path can be point-to-point over public and/or private networks. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN)), Session Initiation Protocol (SIP), wireless network, point-to-point network, star network, token ring network, hub network, Internet, inclusive of the mobile Internet, via protocols such as EDGE, 3G, 4G LTE, Wi-Fi and WiMAX. The engines or system components of FIG. 1 are implemented by software running on varying types of computing devices. Example devices are a workstation, a server, a computing cluster, a blade server, and a server farm. Additionally, a variety of authorization and authentication techniques, such as username/password, Open Authorization (OAuth), Kerberos, Secured, digital certificates and more, can be used to secure the communications.

Figure 3A:
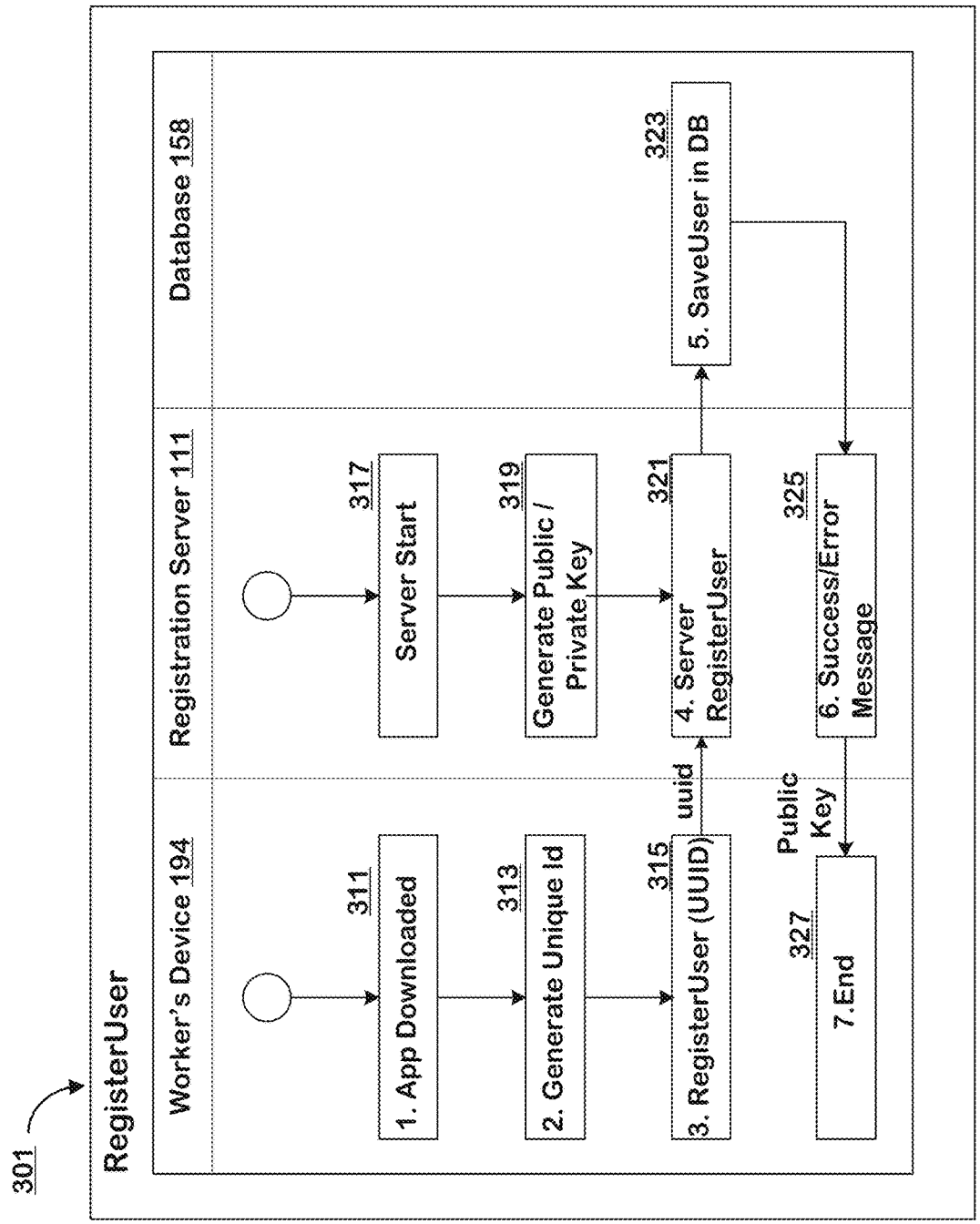
FIGS. 3A, 3B, and 3C present sequence diagrams illustrating the process to set up a user account on an app that can be used to establish authentication credentials and verify health information.
Figure 3B:
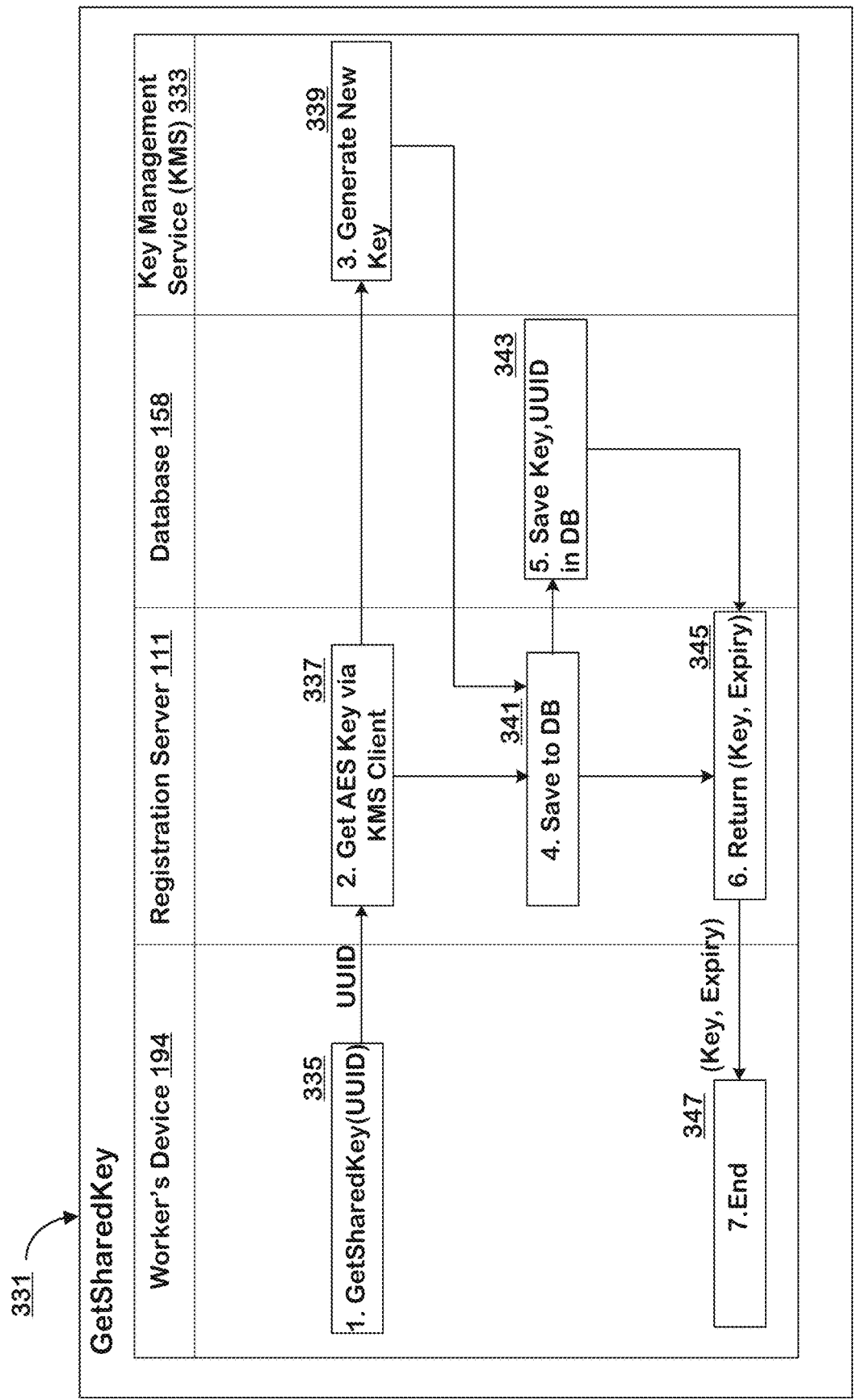
Figure 3C:
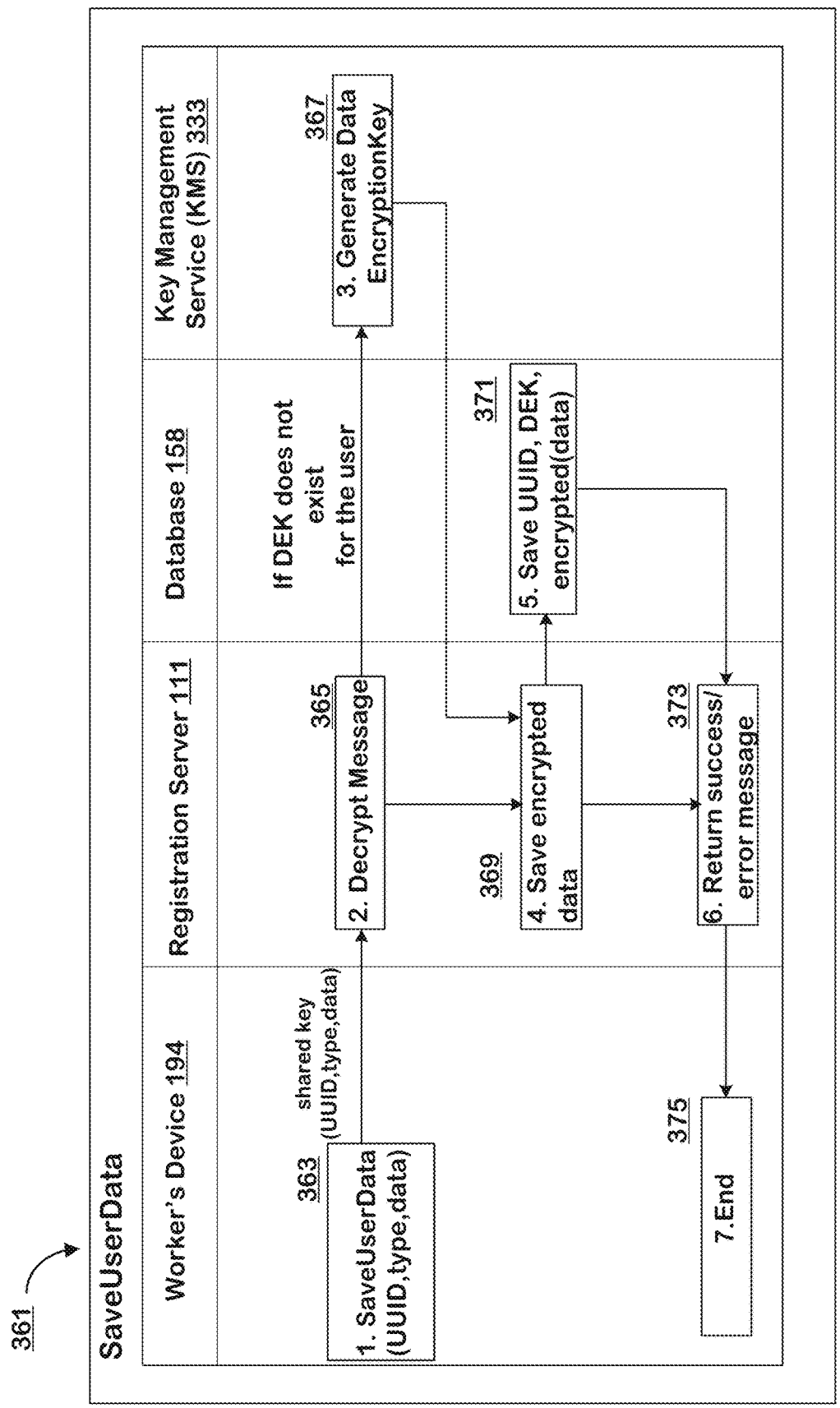

We now present the registration and saving of worker's identification data in the registration workflow, supported by sequence diagrams in FIGS. 3A, 3B, and 3C.

User Registration Workflow

When a worker downloads the app on the worker's device 194, a registration process is performed to register the worker with the registration server 111. FIG. 3A presents a sequence diagram 301 illustrating the registration workflow for registering a worker (or a user). The registration process can involve three actors (or entities) including the worker's device 194, the registration server 111, and the database 158. The worker's device downloads the trustworthy app (311). The app, on the startup, generates a unique user identifier or UUID (313). The UUID may contains a combination of an identifier of the worker's device and a random number generated by the app. The UUID may also be a random number generated by the app without using the identifier of the worker's mobile device. The worker's device sends a message "RegisterUser" to register the UUID with the registration server 111 (315) and passes the UUID to the registration server. The method can also pass the identifier for the worker's device to the registration server.

The registration server starts (317) and generates a public/private key pair (319). The system can use RSA public key cryptosystem to generate the public-private key pair. The registration server receives the UUID and/or the device ID from the worker's device (321). The registration server can store the user's UUID to the database 158 (323). The registration server then sends a success message to the worker's device indicating successful completion of the registration workflow (325). The success message can also include the public key of the registration server. If the registration process is unsuccessful, the registration server sends back an error message to the worker's device including an error code that can indicate an error type (325). The registration process ends when the worker's device receives the success message (327).

We present an example interface that can be used to implement the user registration workflow as described above. Following the interface, we present examples of request and response messages to register a user. The request message includes the UUID of the worker and the response message returns the public key of the registration server and the timestamp when the key was created.

Interface Register User
```
rpc RegisterUser(RegisterUserRequest) returns (RegisterUserResponse) {
    option (google.api.http)={
        // Route to this method from POST requests to/api/
            v1/user:register
        // This returns an Empty message.
        post: "/api/v1/user:register"
        body: "*"
    };
    option
(grpc.gateway.protoc_gen_swagger.options.openapiv2_
    operation)={
    summary: "Post endpoint to Register User"
    description: "Register the user id"
    tags: "User"
    };
}
Message RegisterUserRequest
message RegisterUserRequest {
    // Some user id
    string uuid=1;
}
Message RegisterUserResponse
message RegisterUserResponse {
    // Public key RSA using PKCS1. base64 string
    string pub_key=1;
    // timestamp when the public key was created
    google.protobuf.Timestamp create_time=2;
}
```

Shared Key Exchange

The technology disclosed can use both symmetric encryption and asymmetric encryption for encrypting data and generating signatures. The symmetric encryption uses a shared key to encrypt and decrypt the data. Asymmetric encryption uses a public key of the recipient to encrypt the data and the recipient uses a private key to decrypt the data. Symmetric encryption is a simpler technique, is computationally efficient and fast. Symmetric key is possessed by both parties involved in the communication and hence referred to as a shared key. This key applied to encode and decode the information. Examples of symmetric encryption include AES, DES, RC4, etc. Asymmetric encryption is relatively complex mode of encryption as it involves two cryptographic keys (a public key and a private key) to implement data security. The process of encryption and decryption by two separate keys makes the process slower as compared to use of one shared key. A commonly used asymmetric encryption technique is RSA. The technology disclosed can use both shared and public/private keys to provide a secure communication between worker's device, the registration server, and the verification device. It is understood that one of the two cryptographic techniques (symmetric or asymmetric) can be used for encryption and signing the data.

The worker's device can request a shared encryption key from the registration server to cryptographically encrypt the worker's identification data such as biometric identifier or other personal identification data such as a photograph of the worker. The system can use a shared key in addition to the public encryption of the registration server to provide additional security when sending data to the registration server 111. The shared key is based on the symmetric encryption method in which one key is used for encrypting and decrypting the data. FIG. 3B presents a sequence diagram 331 to get a shared key from the registration server. The process starts when the worker's device sends a "GetSharedKey" message (335) with a UUID to the registration server 111.

The registration server can call a key management service (KMS) 333 to generate the new shared key (337). The KMS can generate a new shared key (339) send the new shared key from the vault to the registration server (341). The registration server can save the shared key to the database 158 along with the UUID for use in decrypting data received from the worker's device (343). The registration server 111 sends the shared key to the worker's device. The registration server can also associate an expiry time with the shared key and include that when sending the shared key to the worker's device (345). The process ends when the worker's device receives the shared key and/or the expiry time from the registration server 111 (347). The registration server can assign a unique symmetric shared key to each registered user using the app. The system can use the Advanced Encryption System (AES) method to generate shared key. In other implementations, the system can use the Diffie-Hellman key exchange method to establish a shared secret key between the worker's device 191 and the registration server 111. This key can then be used to encrypt subsequent communications using a symmetric key cipher (i.e., forward secrecy).

In one implementation, the system can include a key-rotation logic. In such an implementation, the app on the worker's device can check the expiry time of the shared key before sending any data encrypted with the key to the server. If the shared key is about to expire within the next few hours, the client can request a new shared key. This avoids the situation where the scannable code is generated using the shared key and the key expires before the process for verification of the requested user is complete.

We present an example interface that can be used to implement a method to get a shared key from the registration server. We also present an example of a shared key request message that includes the UUID of the worker and an example of a shared key response message that returns the shared key along with a shared key creation timestamp and an expiry timestamp.

Interface GetSharedKey
   rpc GetShared Key (Shared KeyRequest) returns (Shared KeyResponse) {
     option (google.api.http)={
     // Route to this method from GET requests to/api/v1/server:sharedkey
     // This returns the server version
     get: "/api/v1/server:sharedkey"
     };
     option   (grpc.gateway.protoc_gen_swagger.options.openapiv2_operation)={
     summary: "Get Shared Key from the server"
     description: "Generate an AES key in the backend and send it back to the client"
     tags: "Key"
     };
}
Message SharedKeyRequest
message Shared KeyRequest {
   // Some user id
   string uuid=1;
}
Message SharedKeyResponse
message Shared KeyResponse {
   string key=1;
   // timestamp when the shared key was created
   google.protobuf.Timestamp create_time=2;
   // timestamp when the shared key expires
   google.protobuf.Timestamp expires_at =3;
}

Diffie-Hellman Key Exchange

An alternative technique, known as Diffie-Hellman key exchange, can be used to establish shared key between a worker's device and the registration server. The shared key is established using locally generated private numbers at each party (worker's device and registration server) that are never transmitted to the other party. The shared key is calculated locally and not sent to the other party involved in setting up of the key. The shared key can be used by each party to decrypt messages from the other party. Diffie-Hellman key exchange method can be used to achieve forward secrecy. Protocols that achieve forward secrecy generate new shared key for each session that requires encrypted communication and discard them at the end of the session. Forward secrecy prevents an attacker to decrypt the data from historical or future sessions even if they are able to steal that shared key used in a particular session.

FIG. 5A presents a simple example with small numbers to generate a shared key for encrypting data communication between the worker's device 194 and the registration server 111. Small numbers have been used in the example so that the process steps for shared key generation are easily explained. There are four high level steps as shown in FIG. 5A. Prior to starting the process, both worker's device 194 and the registration server have a randomly generated prime number p and a randomly generated prime number referred to as generator g. The generator g is a smaller number than prime number p. In the example shown in FIG. 5A, the values of p and g are set as 23 and 11, respectively. The example presented in FIG. 5A is based on an example retrieved from the Internet <i.stack.imgur.com/AEx0X.png>.

In step 1, both worker's device and the registration server choose respective secret random numbers "a" and "b". In the example of FIG. 5A, the worker's device chooses a random number a equals 6 and the registration server chooses a random number b equals 5.

In step 2, both worker's device and the registration server calculate their public respective public keys A and B using p, g, and their respective secret numbers a and b. The example calculated on workers device and registration server are shown in respective boxes 552 and 558.

In step 3, the worker's device and the registration server exchange their respective public keys with the other party in the communication. The worker's device receives a value of 5 (for B) from registration server and the registration server receives a value of 9 (for A) from the worker's device.

In step 4, the workers device and registration server compute shared key which can be used to decrypt the communication from the other party. The shared key is calculated using the other party's public computed key in step 2 and received from other party in step 3. The calculation of the shared key (K) is shown in boxes 572 and 582, respectively for the worker's device and the registration server. Note, that the shared key is same for both parties i.e., K equals 8.

Figure 5B:
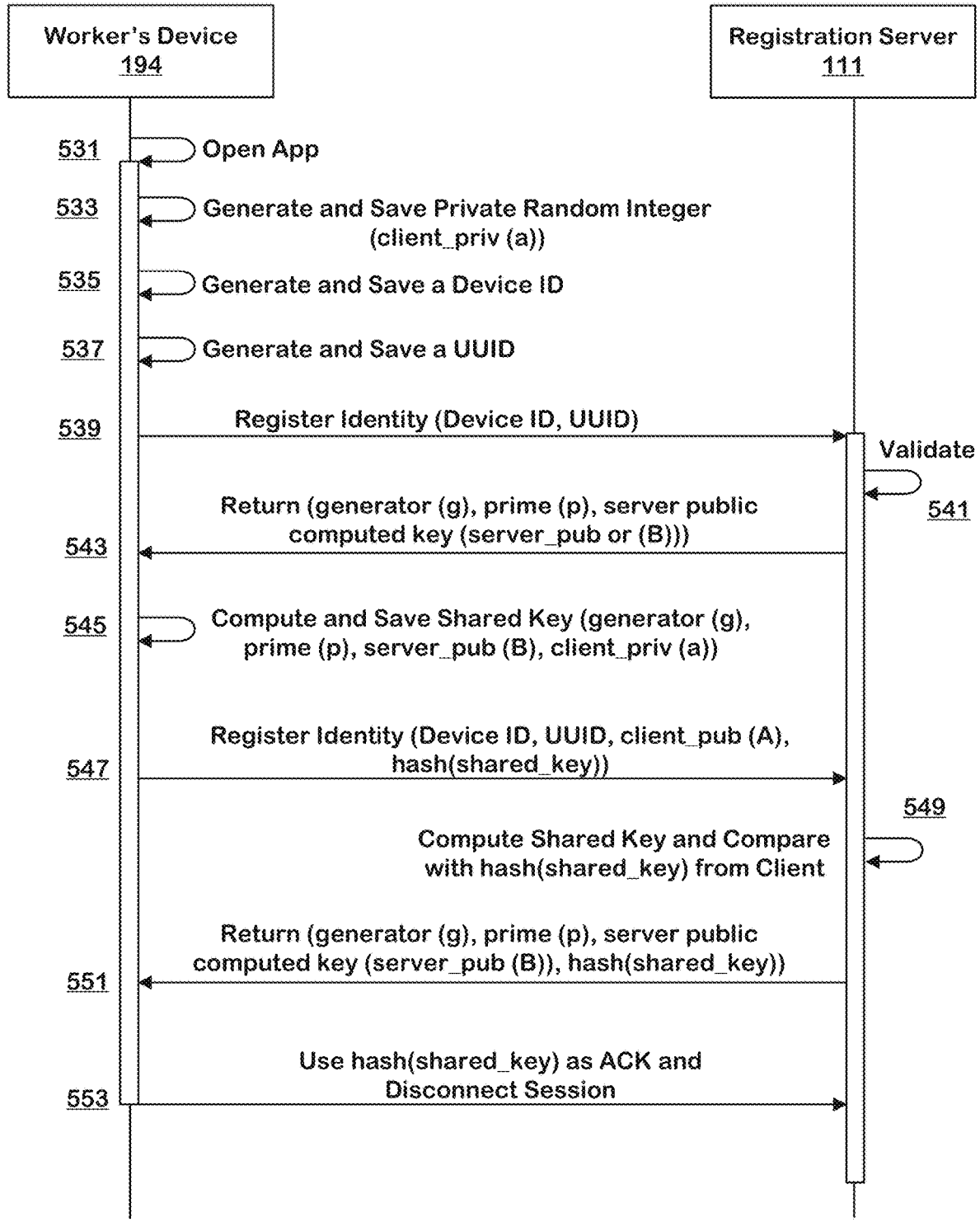
FIG. 5B presents an example sequence diagram for setting up a shared key using the encryption technique of FIG. 5A.

FIG. 5B presents a sequence diagram to set up a shared key for encrypting communication between the worker's device and registration server using Diffie-Hellman method presented in FIG. 5A. The process starts when the worker opens the app on worker's device (such as a mobile phone or a personal digital assistant) 194 as shown in the message 531. The worker's device generates a secret random number "a" also referred to as "client_priv" in message 533. The secret random number "client_priv" is stored locally on the worker's device. The worker's device also stores a device identifier which can also be a randomly generated number or based on a hardware identifier of the worker's device (535). The worker's device generates and stores a unique user identifier (UUID) as shown by a message 537.

The worker's device sends a "register identity" message with to the registration server with the device identifier and the UUID (539). Optionally, the registration server can validate the identity (541). The registration server returns a generator (g), a prime number (p), and a public computed key of server referred to as "B" or "server_pub" (543). The worker's device computes a shared key using the generator (g), the prime number (p), public key of server (server_pub or B) and private key of worker's device (client_priv or a). One example of generating the shared key using above listed data is shown in step 4 in FIG. 5A. The shared key is stored locally on the worker's device and is not sent to the registration server (545). The shared key can be used to decrypt the messages or data received from the registration server.

The worker's device then sends a message "register identity" 547 to registration server. The message can include the device ID, UUID, public key of the worker's device referred to as "client_pub" or "A" and a hash of the shared key referred to as "hash(shared_key)". The registration server computes shared key and compares it with the hash of shared key received from the worker's device (549). The registration server sends a message 551 to the worker's device. The message includes the generator (g), the prime number (p), public computed key of server (server_pub or B) and a hash of the shared key generated by the registration server. The worker's device can send an acknowledgement (or ACK) message to registration server with hash of shared key and disconnect the session (553). At this point, both worker's device and registration server have established a shared key without exchanging the shared key with each other. This shared key can then be used to decrypt any encrypted communication between the registration server and the worker's device.

Save User Data Workflow

FIG. 3C presents a sequence diagram 361 for saving a worker's identification data such as a facial image, name, employee number, etc. in the database 158. The identification data can be accessed by the verification device to match the identification to the worker making a return-to-work request. The trustworthy app on the worker's device sends a message "SaveUserData" with a unique user identifier (UUID), the type of the data, and the data to the registration server 111 (363). The type of the data can be a photograph and/or the name of the worker. The "type" parameter can indicate the type of data being sent e.g., image or photo, name, etc. The "data" parameter can be a Byte or base64 string of data such as a facial image of the worker. The app running on the worker's device 194 can encrypt the UUID, data type, and data parameters using the shared key. The registration server can decrypt the message using the shared key. In one implementation, the UUID is not encrypted with the shared key. The registration server accesses the shared key for the UUID and decrypts the identification data (365).

The registration server can request a data encryption key (DEK) from the key management service (KMS) to encrypt the worker's identification data at rest. The KMS generates a DEK and sends it to the registration server (367). The registration server encrypts the identification data using the DEK (369) and stores the encrypted identification data with the UUID and the DEK in the database 158 (371). The registration server sends a success message 373 to the worker's device 194 after storing the identification data in the database 158 (373). The registration server 111 can send an error message to the worker's device if the identification data is not stored successfully in the database. The error message can contain an error code identifying the error type. The process ends when the worker's device receives the success or the error message (375).

We present an example interface that can be used to implement the save user data to a database. We also present examples of a save user data request message that includes a UUI, a user data type, user data and a flag indicating whether the user data is encrypted. A response message can include a success or error message from the registration server.

Interface SaveUserData
  rpc    SaveUserData(SaveUserDataRequest)    returns (SaveUserDataResponse) {
    option (google.api.http)={
    // Route to this method from POST requests to/api/v1/user:savedata
    //This returns an Empty message.
    post: "/api/v1/user:savedata"
    body: "*"
    };
    option    (grpc.gateway.protoc_gen_swagger.options.openapiv2_operation)={
    summary: "Post endpoint to save user data"

description: "Save user data encrypted in the backend"
tags: "User"
};
}
Message SaveUserDataRequest
message SaveUserDataRequest {
  string uuid=1;
  UserDataType userDataType=2;
  // This is the byte representation of the use data which
  // could be photo or embedding at this point.
  bytes userdata=3;
  // indicates if the userdata field is encrypted
  bool isEncrypted=4;
}
Message SaveUserDataResponse
message SaveUserDataResponse {
  //error message if user data not saved to database
}

We now present sequence diagrams illustrating the generation of scannable code for a worker and scanning of the scannable code by a validator to ensure that a return-to-work request is from an authenticated user.

Scannable Code Generation Workflow

Figure 4A:
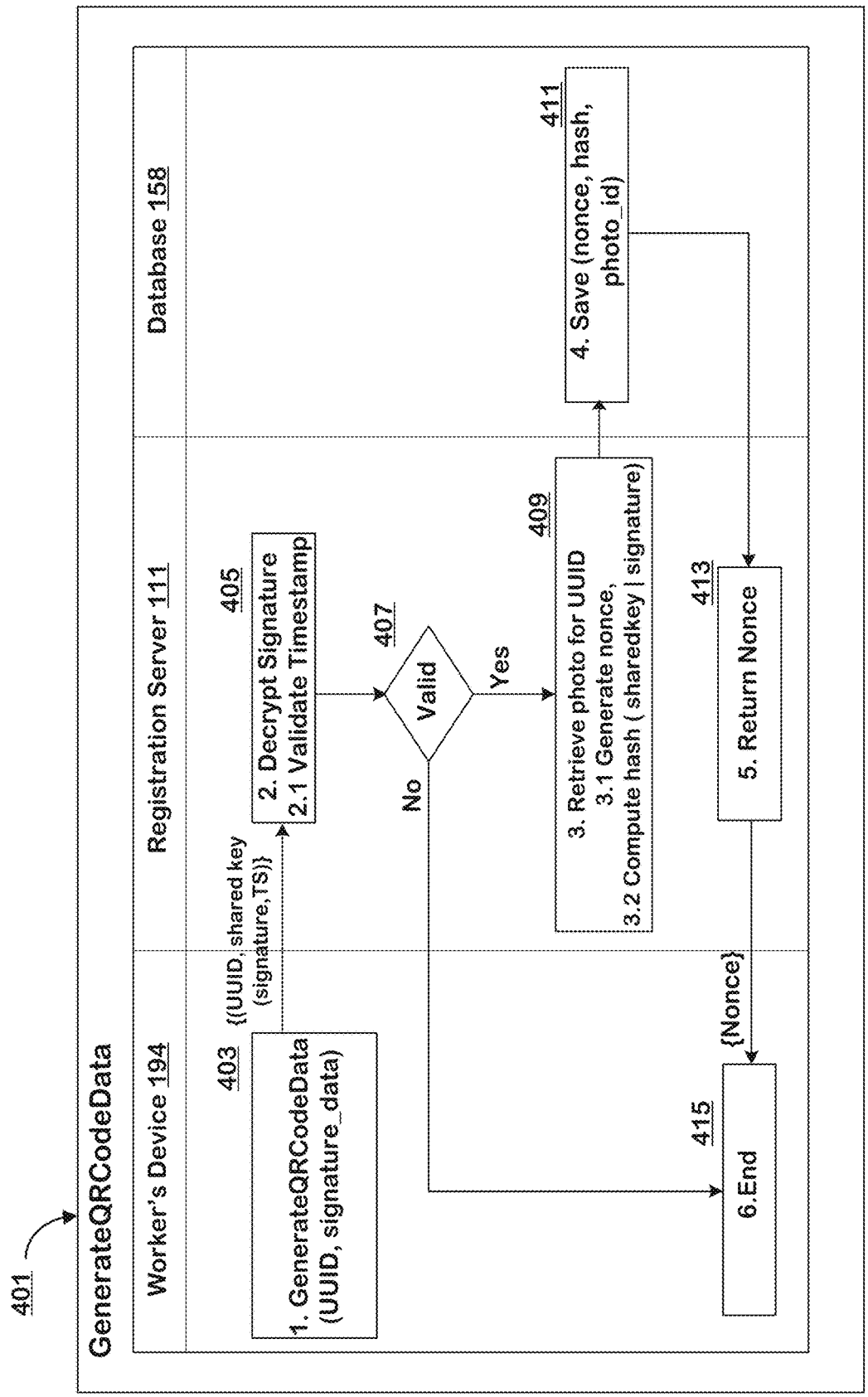
FIG. 4A presents a sequence diagram illustrating the process to generate a scannable code for an authenticated user with verified health information.

FIG. 4A presents a sequence diagram 401 for scannable code generation. The trustworthy app running on the worker's device 194 authenticates the worker before the process to generate the scannable code is initiated. During authentication, a biometric authentication feature vector for the worker is matched to a characteristic identity vector to authenticate the worker. The authentication and characteristic identity vectors are generated using non-deterministic biometrics inputs obtained from the worker such as facial images and voice samples. We present details of generating the biometric identifier in the following sections. The technology disclosed stores the biometric identifiers locally to preserve the privacy of users. Cryptographically signed biometric identifiers can be sent to the registration server for verification of the worker's identity and for use in the generation of scannable code.

The process of generating scannable code starts when the worker's device sends a "GenerateQRCodeData" message to the registration server 111 (403). The message can include a UUID of the user and signature data. The signature data can be a cryptographically signed biometric identifier such as a characteristic identity vector of the authenticated user. The shared encryption key can be used to cryptographically sign the biometric identifier. A timestamp can also be included in the message and encrypted using the shared key of the user. The registration server can decrypt the signature and the timestamp using the shared key (405). The registration server can access the shared key from the database using the UUID of the worker. The registration server can verify the cryptographical signed biometric identifier (or signature) for the user by matching it with a previously stored cryptographically signed biometric identifier (or signature) for the worker. The registration server can validate the timestamp by checking if the timestamp in the request message is created within a pre-defined time limit such as the last one minute or the last 30 seconds or even less than that (407). If the timestamp is not valid and/or the signature is not verified, the registration server can send an error message to the app on the worker's device and the process ends (415). Otherwise, if the timestamp is valid and the cryptographic signature is verified by the registration server then the process continues at step 409.

The registration server retrieves the identification data for the worker from the database 158. An examples of identification data can be a facial image photograph of the worker. The registration server can access the photograph using the UUID of the worker. The registration server then generates a success nonce and computes a hash of the shared key and cryptographic signature of the worker. The success nonce is a one-time code, generated for the scannable code and may not be used for another scannable code. The success nonce can be a random number. For example, a success nonce can be a 256-bit integer. Various sizes of integers with more or less bits than 256 can be used. A part of the success nonce can also include timestamp data. The above process steps are illustrated in a box labeled 409 in the sequence diagram 401. The registration server then saves a triplet of the success nonce, hash and the photo identifier for the worker in the database 158 (411). The hash of the cryptographic signature of the worker can be generated by applying a hash function such as 256-bit sha3. In one instance, the hash of the shared key and the cryptographic signature of the worker is generated by applying the hash function. Other hashing functions such as 512-bit sha3 can also be applied to generate a hash.

The registration server sends the success nonce to the worker's device after completing the storage of the triplet to the database (413). The app on the worker's device recreates or recomputes the hash of the cryptographic signature using the same hash function as used by the registration server 111. If the registration server computed the hash of the shared key and the cryptographic signature the worker's device also calculates the hash of both the shared key and the cryptographic signature. The worker's device then encrypts the success nonce and the hash using the public key of the registration server. The encrypted data is then displayed as a scannable code such as a quick response (or QR) code 211 on the user interface of the worker's device and the process ends (415). The scannable code can be sent to a verification device 114 to get approval to return to work. The verification device can be operated by a representative of the employer.

We present an example interface that can be used to implement the scannable code generation logic described above. A signature data message is also presented that includes a worker's signature data. An example request message to generate QR code data is presented that includes encrypted signature data. An example response message is also presented that includes a success nonce that can be used once in the cryptographic communication.

Interface GenerateQRCodeData
rpc    GeneratorQRCodeData(GenerateQRCodeDataRequest) returns
(GenerateQRCodeDataResponse) {
  option (google.api.http)={
    // Route to this method from POST requests to/api/
      v1/qrcodedata:generate
    post: "/api/v1/qrcodedata:generate",
    body: "*"
  };
  option    (grpc.gateway.protoc_gen_swagger.options.
    openapiv2_operation)={
    summary: "Generate the data for the QR code"
    description: "Generate the QR code data based on
      the information passed by the client"
    tags: "QR-Code-data"
  };
}
Message SignatureData
message SignatureData {

```
// Arbitrary signature data in base64 string
    bytes data=1;
    // Epoch time (seconds) when this request was gener-
       ated.
    int64 epoch_time=2;
}
Message GenerateQRCodeDataRequest
    string uuid=1;
    // encrypted bytes for message SignatureData
    bytes signature_data=2;
}
Message Generate QRCodeDataResponse
    //Some randomly generated id to identify request in logs
    string id=1;
    // a nonce is an arbitrary number that can be used just once
       in a cryptographic communication
    string nonce=2;
    // timestamp when the public_key was created
    google.protobuf.Timestamp create_time=3;
}
```

Scannable Code Validation Workflow

Figure 4B:
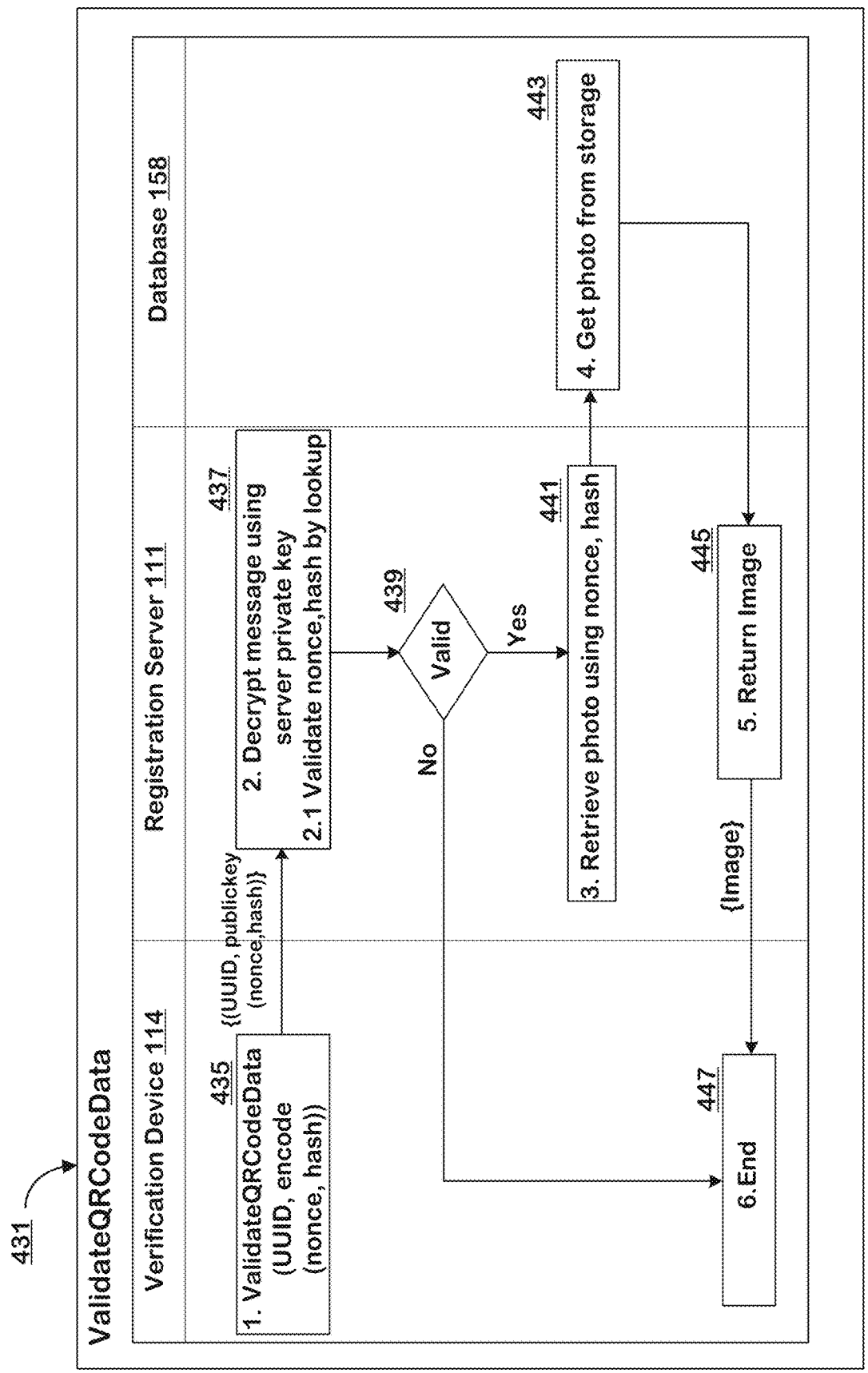
FIG. 4B presents a sequence diagram illustrating the process for verifying by a validator upon scanning of the scannable code that the request is sent by an authenticated user.

FIG. 4B presents a sequence diagram 431 for validation of a scannable code by the verification device 114. The verification device 114 scans the scannable code generated by the worker's device. The verification device may scan the scannable code displayed on the user interface of the worker's device 194. In one implementation, the worker's device 194 may electronically send the scannable code to the verification device 114. Upon scanning the scannable code, the verification device 114 sends a "validateQRCodeData" message to the registration server 111 and passes the UUID of the validator along with the scannable code data. The scannable code data can include a nonce code (or success code) and hash, encrypted using the public encryption key of the registration server 111 (435). The registration server can decrypt the message using private key and validate the nonce code and hash by matching the nonce and hash in the database 158 (437). If the nonce code and hash are valid, the two data elements match the triplet of success nonce, hash and photo identifer saved in the database 158 during the generation of the scannable code for the worker (439). If the nonce and hash do not match a triplet stored in the database, then the registration server can send an error message to the verification device (447).

The registration server 111 can retrieve the photo identifier from the matching triplet retrieved from the database and access the database to retrieve the photograph of the requesting worker (443). In one implementation, one data element such as the nonce code and/or hash can be used to access the photograph identifier of the worker from the database 158. The photograph identifier can be used to retrieve the photograph (441). In one implementation, the nonce and hash can be used to retrieve the photograph from the database 158. The photograph is then sent to the verification device 114 (445) for display on the user interface of the verification device 114. The employer or a representative of the employer can visually match the photograph of the worker from the registration server to the photograph displayed on the app on the worker's device to determine that the request is from an authenticated worker (447). The representative of the employer can also match the photograph from the registration server to the worker presenting the request to return to work to determine that the request is from an authenticated user. The system can also store the employee's name, employee identification number or other identification information with the facial image data of the worker for verification purposes.

We present an example interface that can be used to implement the logic to validate the scannable code. An example QR code data message is presented that includes the nonce code and hash of the shared key and the signature of the user. Examples of request and response messages to validate the scannable code are also presented.

```
Interface ValidateQRCodeData
    rpc ValidateQRCodeData (ValidateQRCodeDataRequest)
       returns
    (ValidateQRCodeDataResponse) {
        option (google.api.http)={
            // Route to this method from POST requests to
               /api/v1/qrcodedata:validate
            post: "/api/v1/qrcodedata:validate",
            body: "*"
        };
        option    (grpc.gateway.protoc_gen_swagger.options.
            openapiv2_operation)={
            summary: "Validate the data from the QR code"
            description: "Endpoint to validate the QR code data
               sent by the client"
            tags: "QR-Code-data"
        };
}
Message QRCodeData
message QRCodeData {
    // nonce was generated by the GenerateQRCodeData
       step
    string nonce=1;
    // hash is generated locally on the phone using
       sha256.Sum256(shardkey, signature)
    string hash=2;
}
Message ValidateQRCodeDataRequest
message ValidateQRCodeDataRequest {
    string uuid=1;
    // binary data encrypted pubkey server QRCodeData
    bytes validation_data=2;
}
Message ValidateQRCodeDataResponse
message ValidateQRCodeDataResponse {
    // Some randomly generated id to identify request in
       logs
    string id=1;
    // type of data
    UserDataType userDataType=2;
    // This is the byte representation of the use data which
    // could be photo or embedding at this point.
    bytes userdata=3;
}
```

We now present the use of non-deterministic biometric inputs to establish authentication credentials such as a characteristic identity vector for the worker.

Characteristic Identity Vector

Figure 6A:
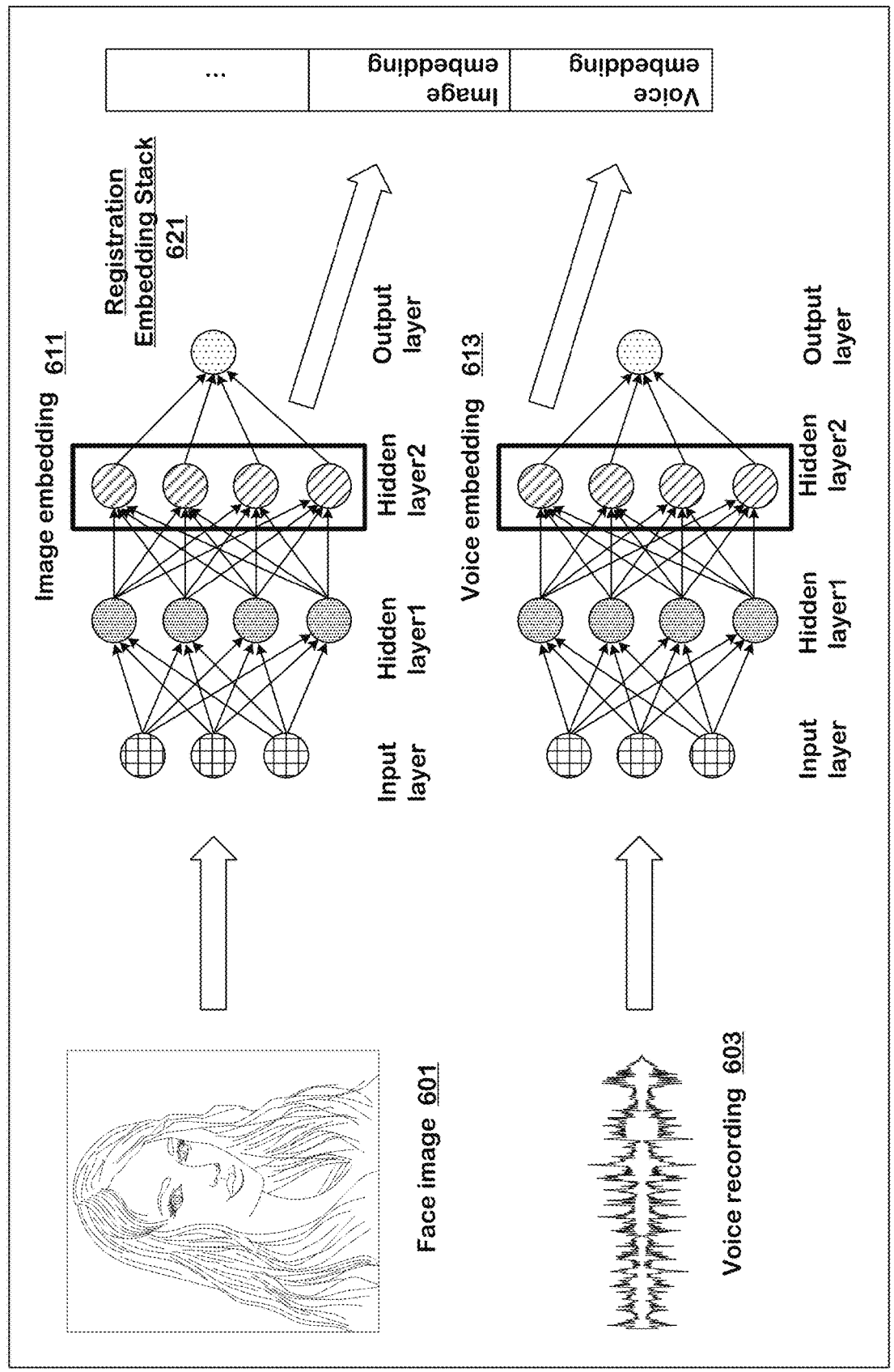
FIG. 6A presents processing of non-deterministic biometric inputs using machine learning models to generate feature vectors.

The system can use non-deterministic biometric inputs such as voice and face images to generate a characteristic identity vector, against which authentication input is measured. Biometric inputs are variable and can thus result in the generation of non-deterministic features which make it difficult to authenticate the user. The technology disclosed can generate a characteristic identity vector to represent a worker (or a user) using a plurality of biometric inputs. FIG. 6A presents an example of generating a feature vector using a facial image 601 and a voice sample 603 of the worker. A single biometric input such as the facial image or the voice sample can be used to generate an identity feature vector. A set of biometric inputs including a facial image and a voice sample can also be used to generate an identity feature vector. The system can use additional inputs such as the location history of the worker or the genomics data of the worker to generate identity features.

The system can use a variety of trained machine learning models to generate features. In one example, the facial image data is fed to a trained ArcFace machine learning model (available at www.arxiv.org/abs/1801.07698). The embeddings generated by the model in the second-to-last layer (hidden layer) are used as a registration feature vector. Other examples of machine learning models that can be used to generate feature vectors from facial images include ImageNet, VGG Face (available at www.robots.ox.ac.uk/~vgg/software/vgg_face/), Phenomenal Face model, Happy Face model, etc. The ArcFace model performed better in some cases than other models due to its Additive Angular Margin Loss which optimizes for neighborhoods of similar facial identities. The model was pre-trained on a large image dataset. The diagram of a machine learning model architecture in FIG. 6A shows an input layer, a hidden layer 1, a hidden layer 2 and an output layer. The example architecture shows a fully connected (FC) network. However, it is understood that convolutional neural networks (CNNs) can be used for generating embeddings. In a convolutional layer, each neuron is only connected to a few nearby (or local) neurons in the previous layer. CNNs are commonly used for extracting features from image data as the features are local (e.g., nose, eyes, etc.) and can occur anywhere in the image.

The system can also feed a voice sample from the worker to trained machine learning models to generate registration feature vectors. Examples of trained machine learning models that can be used to process voice samples include VladNet (available at arxiv.org/pdf/1902.10107.pdf), VGG Vox (available at www.robots.ox.ac.uk/~vgg/publications/2018/Chung18a/chung18a.pdf), etc. The system can provide a plurality of voice samples (or utterances) from the user to a trained model such as VladNet. The voice embedding 613 output by the second-to-last layer of the model are stacked with the image embedding 611 to generate a registration feature vector 621 (or registration embedding stack) for the worker. The system can generate a plurality of registration feature vectors by using a plurality of facial images and corresponding voice samples.

Figure 6B:
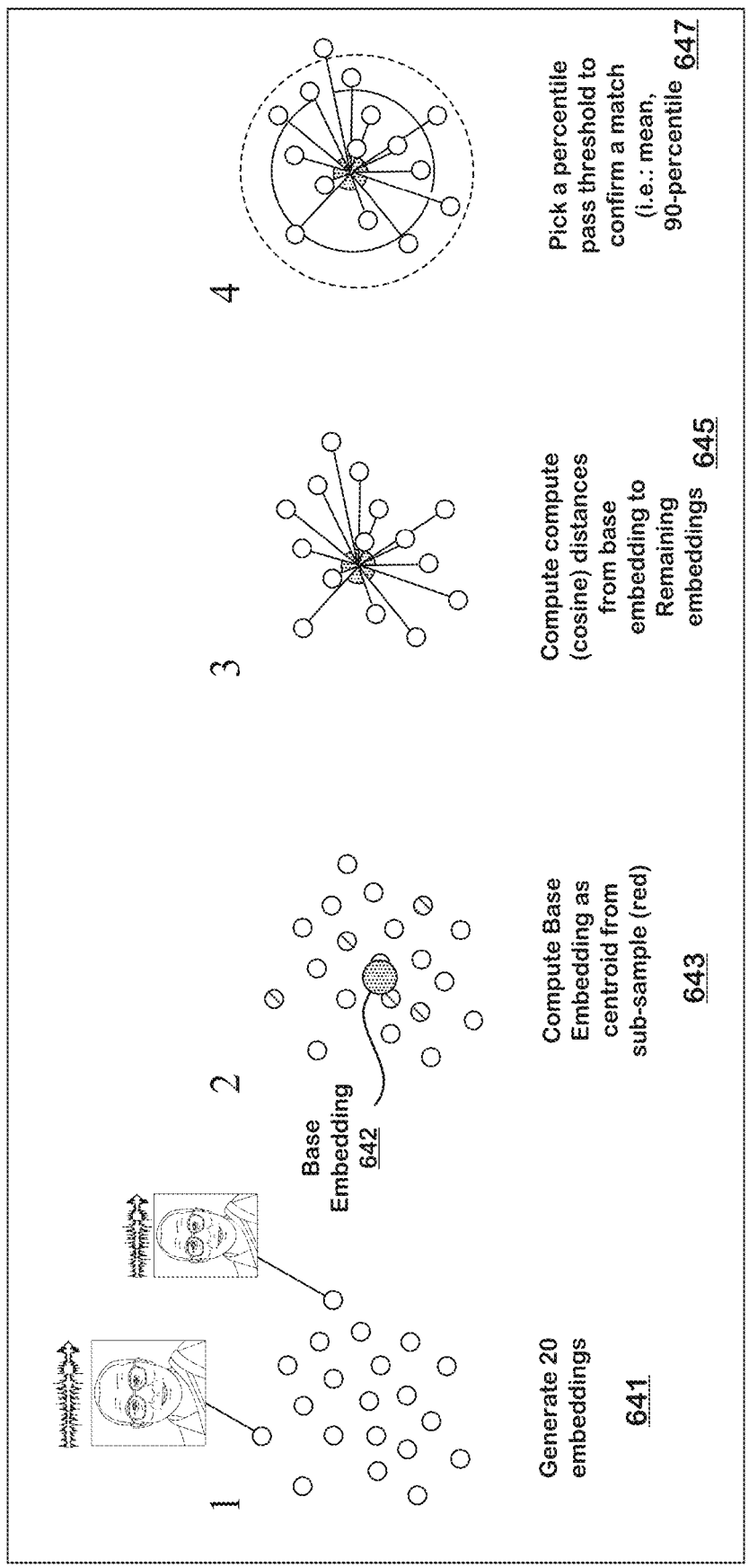
FIG. 6B presents computing of a characteristic identity vector representing the user from a plurality of feature vectors.

FIG. 6B presents one approach that can be applied by the characteristic identity vector generator 133 to generate a characteristic identity vector from the plurality of registration feature vectors generated as described above. The system generates a plurality of registration embeddings or registration feature vectors by using sets of biometric inputs. As shown in the example in FIG. 6B, the system generates twenty registration embedding 641 by using twenty sets of biometric inputs. Each set of input can include a facial image and a voice sample. The set can also include additional inputs such as location, genomics data, etc. More than twenty embeddings can be generated during registration of the user with the trustworthy app.

A base embedding (or characteristic identity vector or characteristic feature vector) is generated by using a subset of the embeddings 641. In one instance, five embeddings (shaded circles) can be used to generate a base embedding by averaging the five embeddings (643). More than five embeddings can be used to generate the base embedding. A distance is calculated for each of the remaining fifteen embeddings to the base embedding. In one instance the embeddings or feature vectors are mapped to the surface of a unit hyper-sphere. As all the feature vectors have a unit length, a cosine distance between the embeddings can be calculated as shown in illustration 645. Other distance metrics can be used to calculate the distance between the base embedding and other registration embeddings.

A threshold can be selected to match an authentication or login embedding and the base embedding. For example, as shown in FIG. 6B, the threshold relative to the 90th-percentile of distances is set (647). This threshold means that if the login or authentication embedding is within a distance from the base embedding in which 90 percent of embeddings are positioned then the login is accepted as a match and the user is authenticated. Different values of thresholds such as 70th-percentile, 80th-percentile, etc. can be used. If a user has more variation in biometric inputs then their registration embeddings can be more spread out. The threshold distance for such users will be greater to match the login embeddings to the base embedding. The details of matching the authentication feature vector to the characteristic identity vector to authenticate the worker are presented below.

Authentication Identity Vector

Figure 6C:
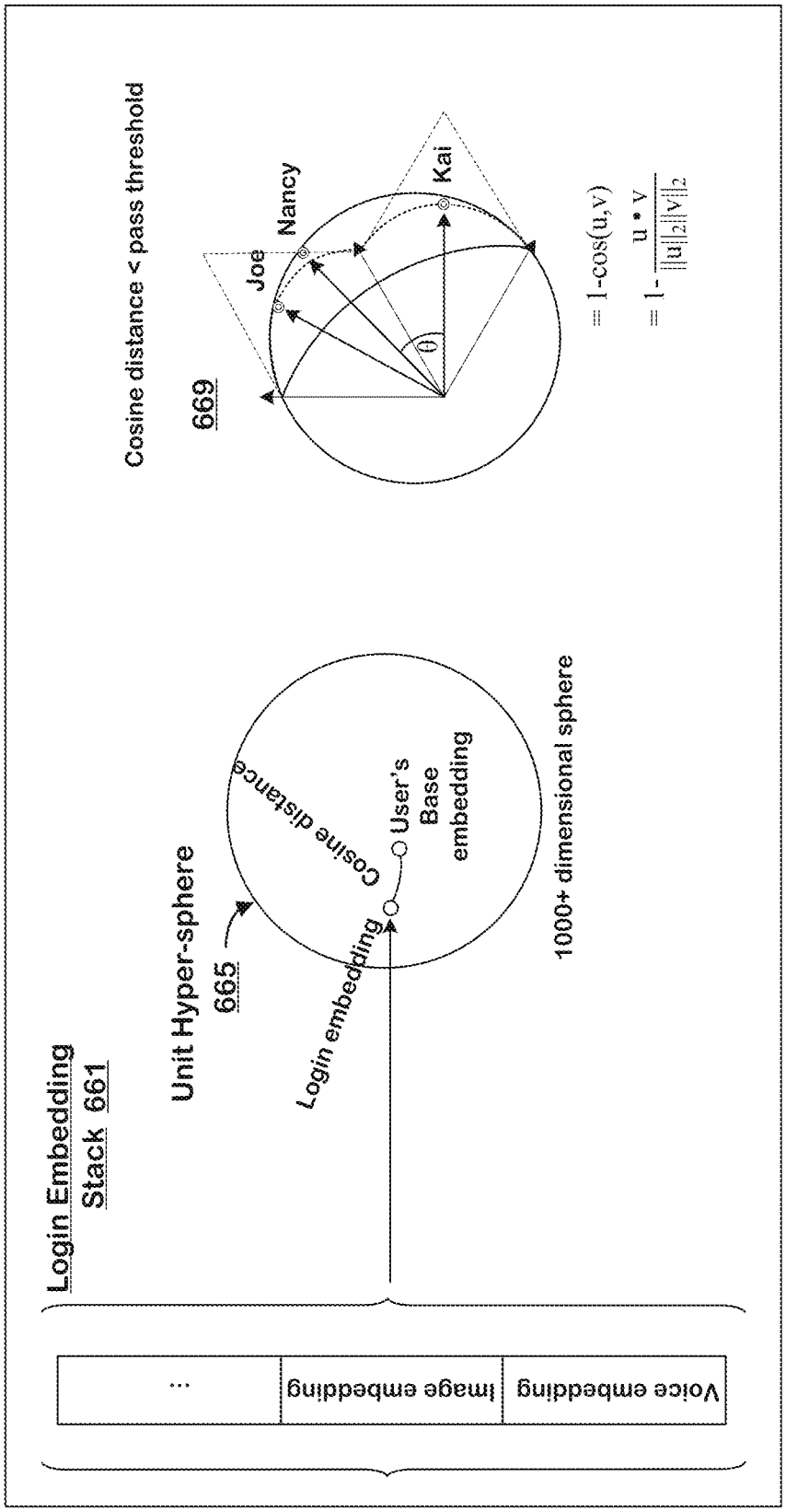
FIG. 6C presents authentication of a user by using an authentication feature vector generated from non-deterministic biometric inputs.
Figure 6D:
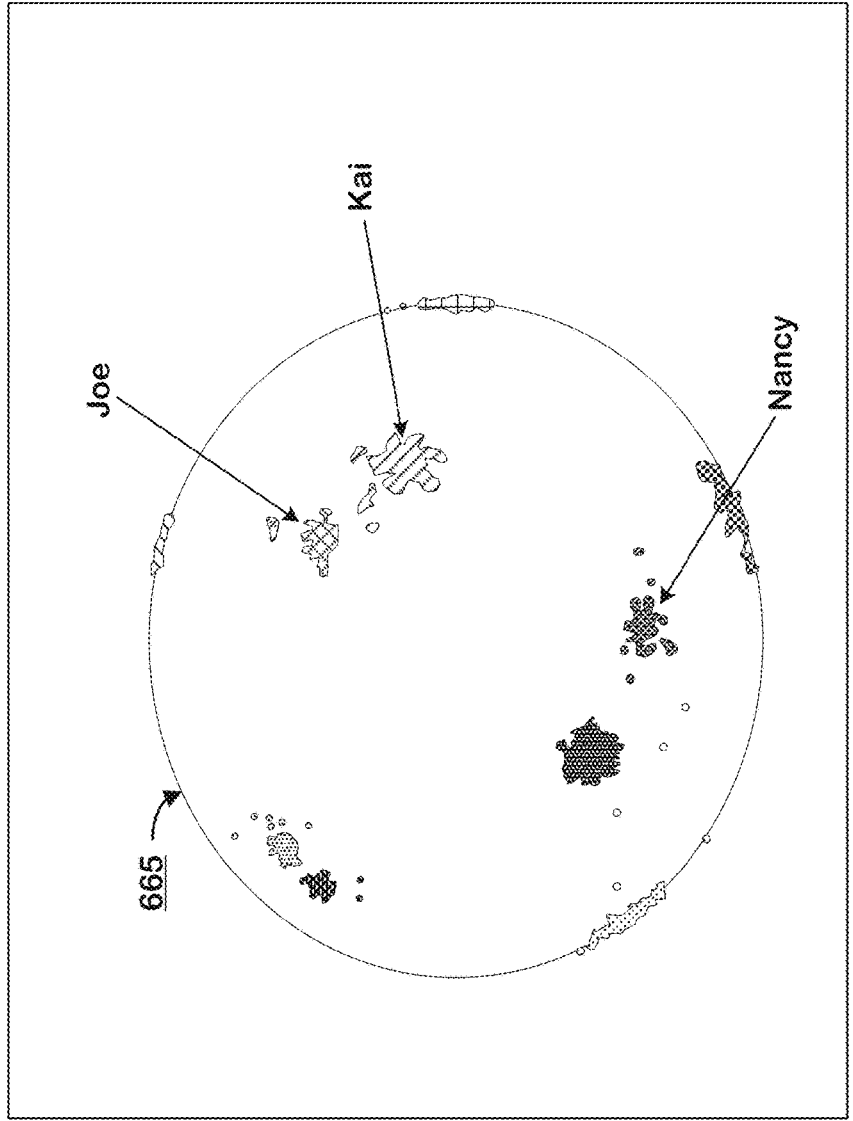
FIG. 6D presents an illustration of clusters of feature vectors of users positioned on the surface of a unit hyper-sphere.

The authentication identity vector (or login embedding) can be generated using the same pre-trained machine learning models as are used to generate the registration feature vectors. FIG. 6C shows a login embedding 661 that includes stacked image and voice embeddings. The authentication identity vector is mapped to the unit hyper-sphere 665 and a cosine distance between the authentication identity vector and the characteristic feature vector (or user's base embedding) is calculated. The distance can be calculated using the cosine distance between the two vectors. If the calculated distance is less than the pre-determined threshold, the user is authenticated. The illustration 669 shows base embeddings of three example users Joe, Nancy and Kai, mapped to the unit hyper-sphere. The unit hyper-sphere is a high dimensional sphere that can have up to one thousand or more dimensions. FIG. 6D illustrates clusters of registration feature vectors of the three users mapped to the surface of the unit hyper-sphere 665. We now present examples of collecting biometric inputs from users and pre-processing these inputs for the generation of registration and authentication feature vectors.

Process Flowchart for Authenticating a User

Figure 6E:
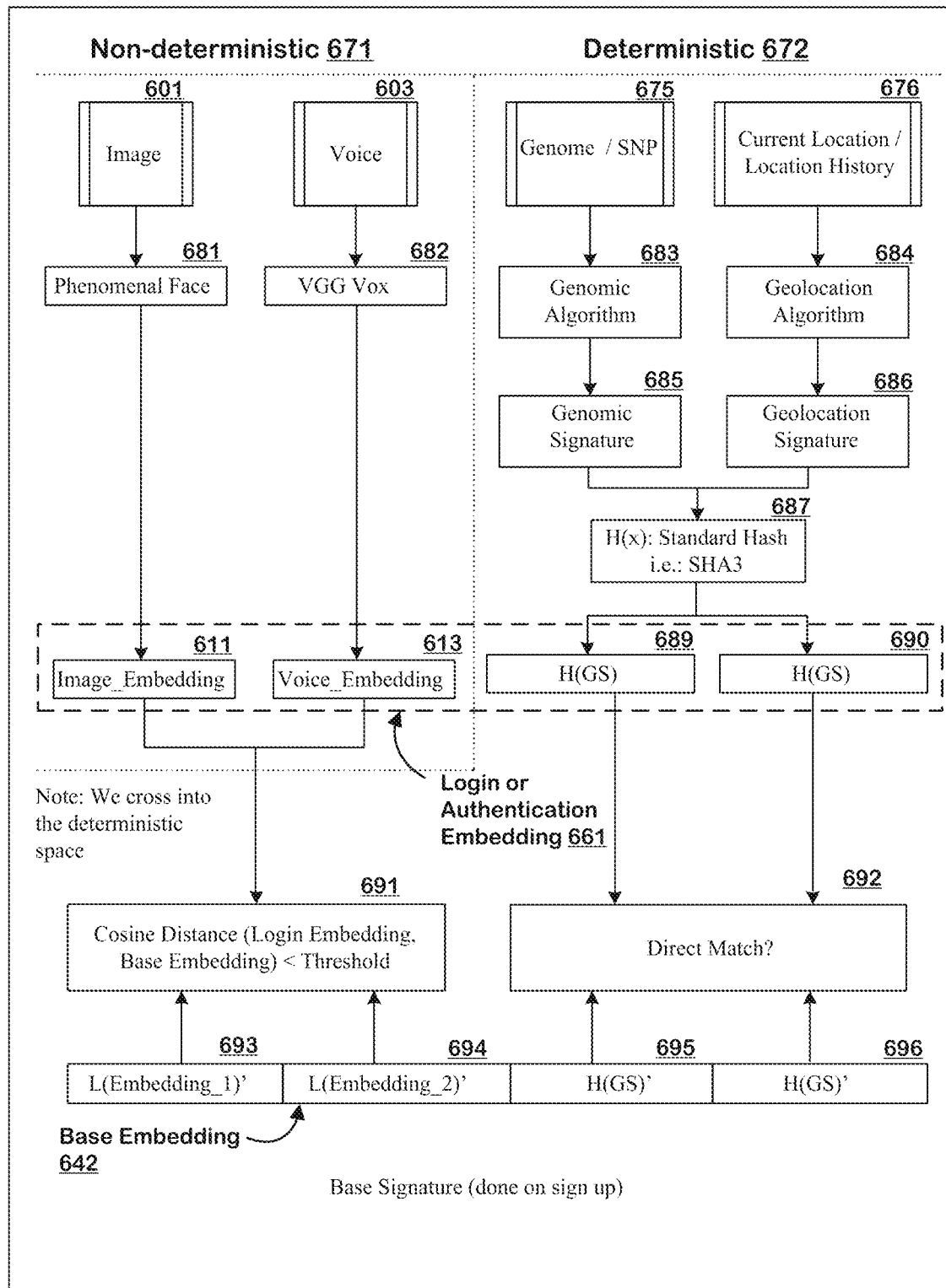
FIG. 6E presents a process flowchart for authenticating a user by calculating a cosine distance between an authentication feature vector and a characteristic identity vector.

FIG. 6E presents a process flowchart for authenticating a user by calculating the cosine distance between the authentication feature vector and the characteristic identity vector. The process starts by providing non-deterministic input 671 to machine learning models. The non-deterministic inputs can include a facial image 601 and a voice sample 603. Trained machine learning models 681 and 682 process the inputs to generate image and voice embeddings 611 and 613, respectively. A variety of trained machine learning models can be applied, the Phenomenal Face (681) and VGG Vox (682) models are shown as examples. More examples of machine learning models that be applied to non-deterministic inputs are presented with reference to FIG. 8A.

The system can optionally include deterministic inputs 672 for authenticating the user. Examples of deterministic inputs include location history of the user or genomic data of the user. The system can extract a genomic signature (685) from the user's genomic data (675) by analyzing specific patterns and substrings of the sequencing data and/or SNPs (683). The current location or location history of the user (676) can also be used to generate a geolocation signature 686 by applying a geolocation algorithm 684. The geolocation algorithm can use the current location or location history of the user to generate latitude and longitude values that can be used as a geolocation signature. The genomic and location inputs are deterministic i.e., the same output is obtained for given input values. The system can apply a standard hash (687) to genomic and geolocation signatures to generate hashes 689 and 690, respectively. Hashing algorithm such as SHA3 can be applied to generate hashes.

An authentication feature vector 661 (or authentication embedding or login embedding) is generated by combining the embeddings 611, 613 and hashes 689 and 690. The system can authenticate the user by direct matching (692) the deterministic parts (689 and 690) of the login embedding 661 with respective hashes (695 and 696) in base embedding 642. The non-deterministic part (611 and 613) of the login embeddings are matched to corresponding embeddings (693 and 694) in base embedding 642 by calculating a cosine distance between the login and the base embeddings at a step 691. The distance calculated can be compared to a threshold to authenticate the user. If the distance is less than the threshold, the user is authenticated.

Capturing and Pre-Processing Biometric Inputs

Figure 7A:
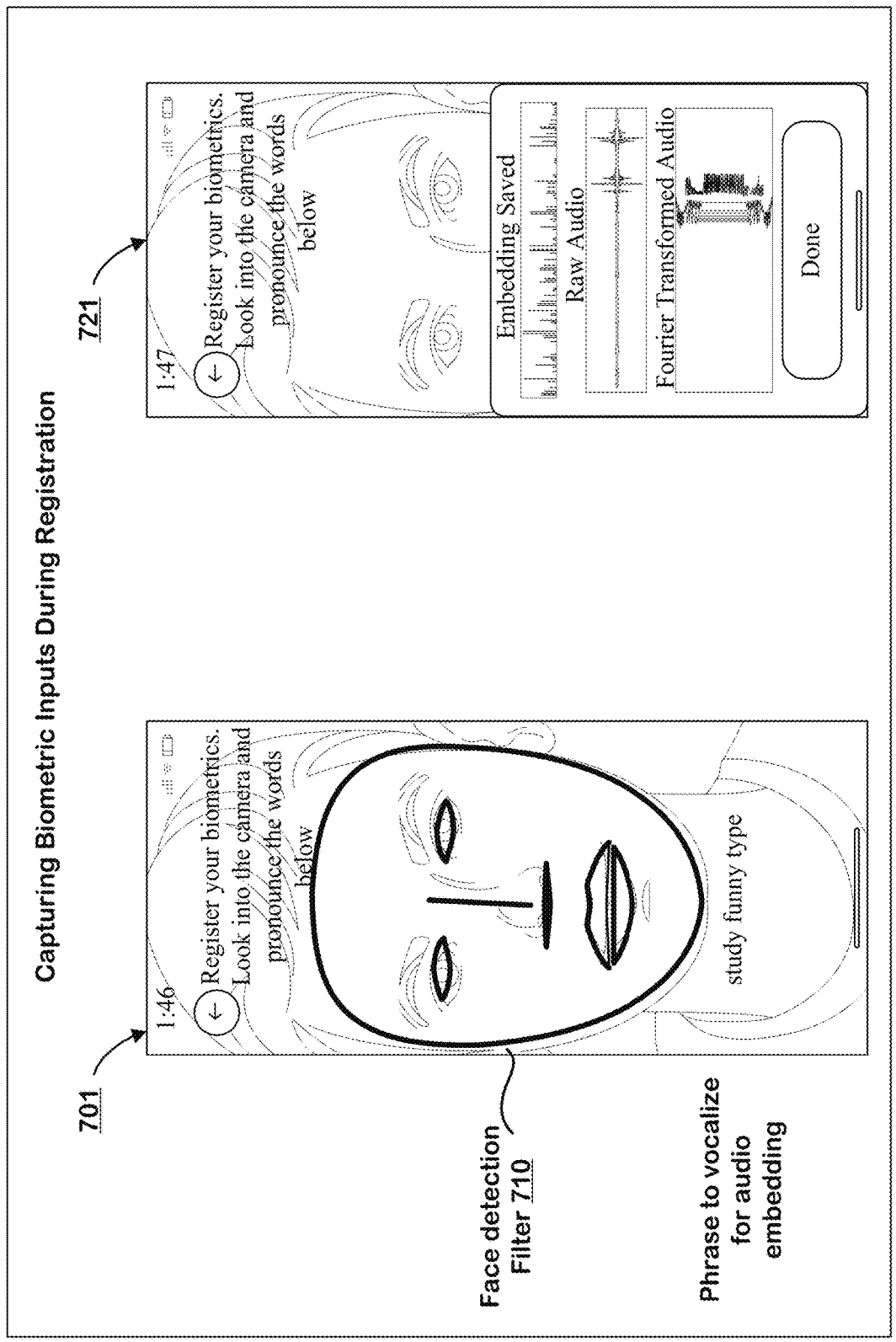
FIG. 7A presents an example user interface for capturing biometric inputs including a facial image and a voice sample of a user during registration.

FIG. 7A presents an example user interface 701 of the app running on a worker's device that can be used to capture biometric inputs. The app can apply a face detection filter 710 to detect that a face image is present in the selfie image captured from the camera of the worker's device. The user is provided a phrase to pronounce on the user interface. A sound sample is captured when the user utters the phrase presented on the user interface 701. The app can present different phrases when capturing biometric inputs. A plurality of sets of face images and voice samples is then processed to generate a plurality of registration identity vectors. The user interface 721 presents the user interface message when a registration identity vector or registration embedding is saved. The system can display the image, raw sound sample and processed sound sample. The user can press the "Done" button on the user interface 721 to accept the biometric input.

Figure 7B:
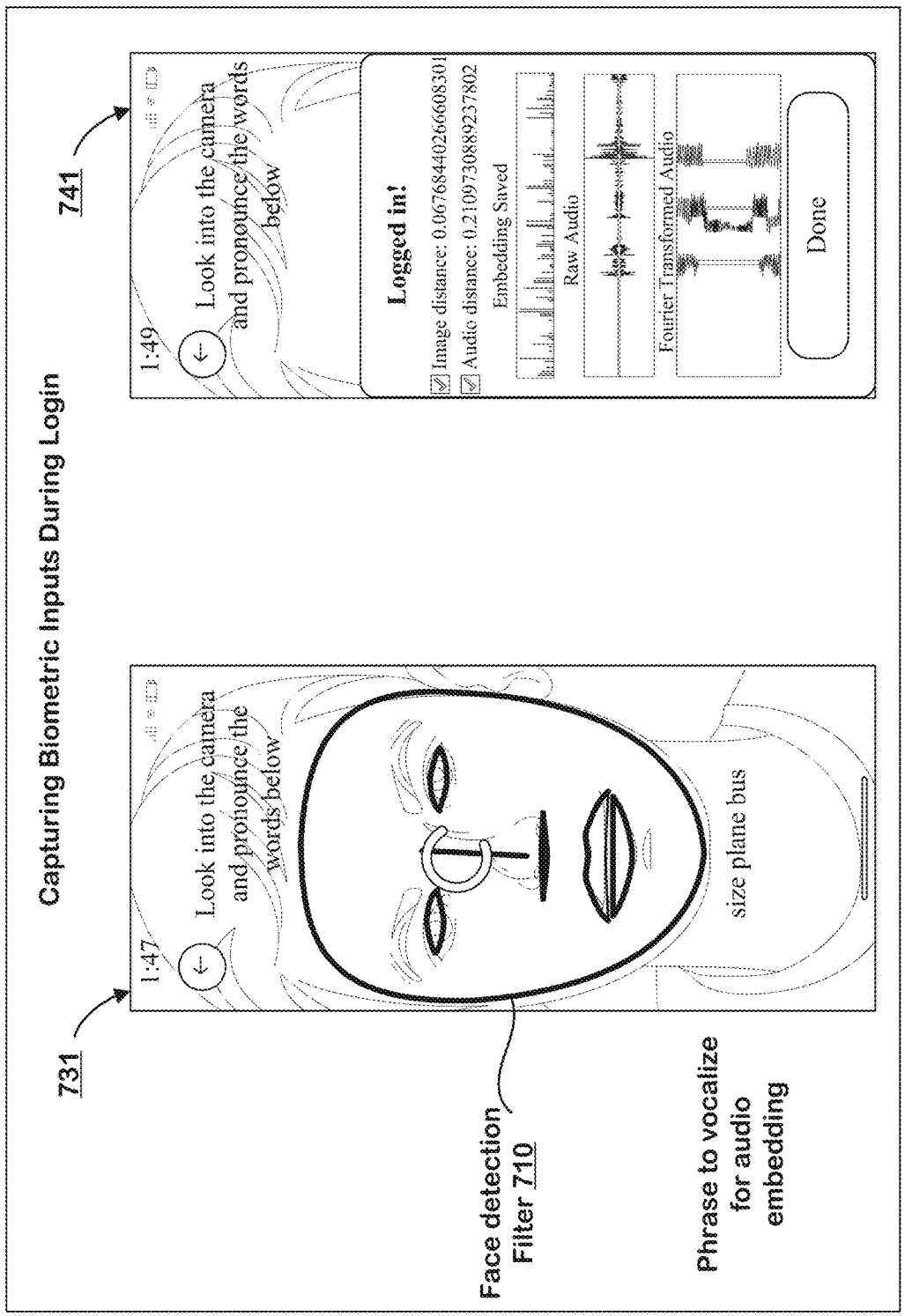
FIG. 7B presents an example user interface for capturing biometric inputs including a facial image and a voice sample of a user during login.

FIG. 7B presents a user interface example 731 to capture biometric inputs including a facial image and sound sample during login. A face detection filter 710 can be used to detect the face image in the photograph captured by the camera. The system provides a phrase that can be different from the one used in the registration process to capture a voice sample from the user. The system can apply the logic described above to match the login embedding to the base embedding generated during the registration process. If the distance between the base embedding and the registration embedding is less than a pre-determined distance, the user is logged in to the app as shown in user interface example 741. The user can press the "Done" button to continue using the trustworthy app after the authentication process is complete.

Figure 7C:
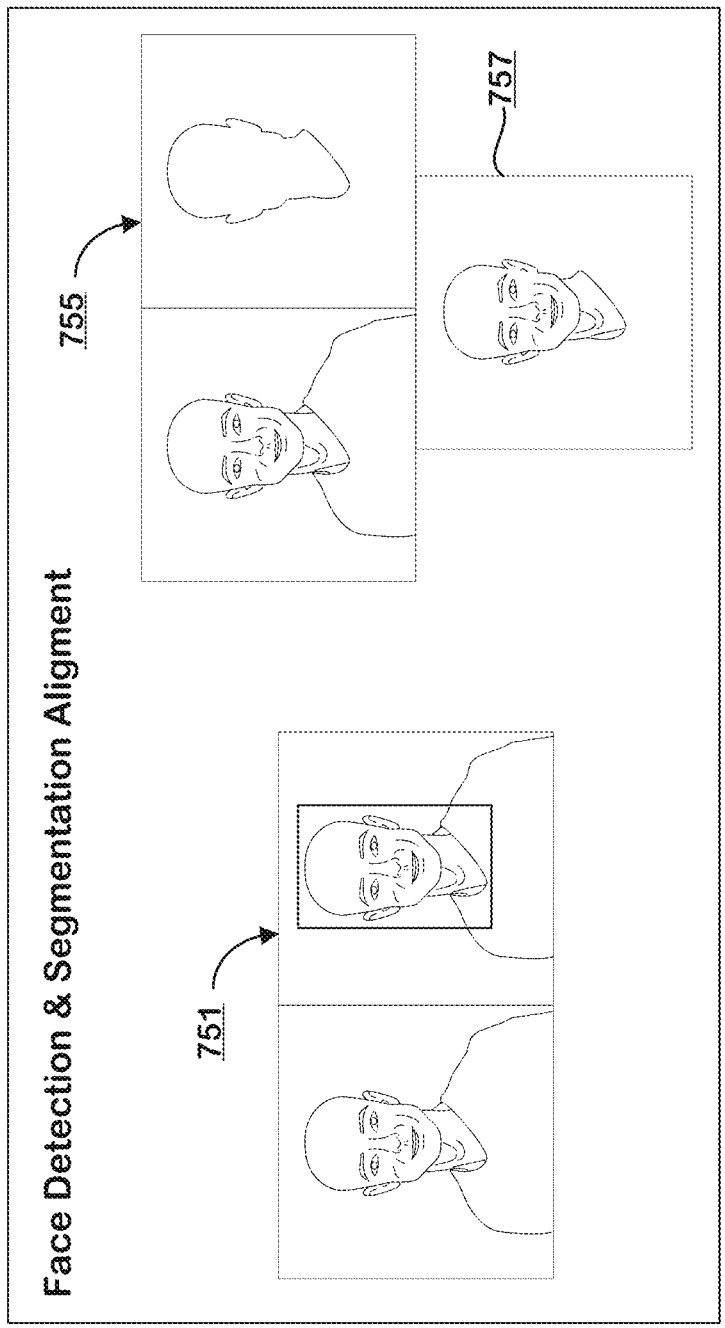
FIG. 7C presents examples of pre-processing of facial images including segmentation and background removal.
Figure 7D:
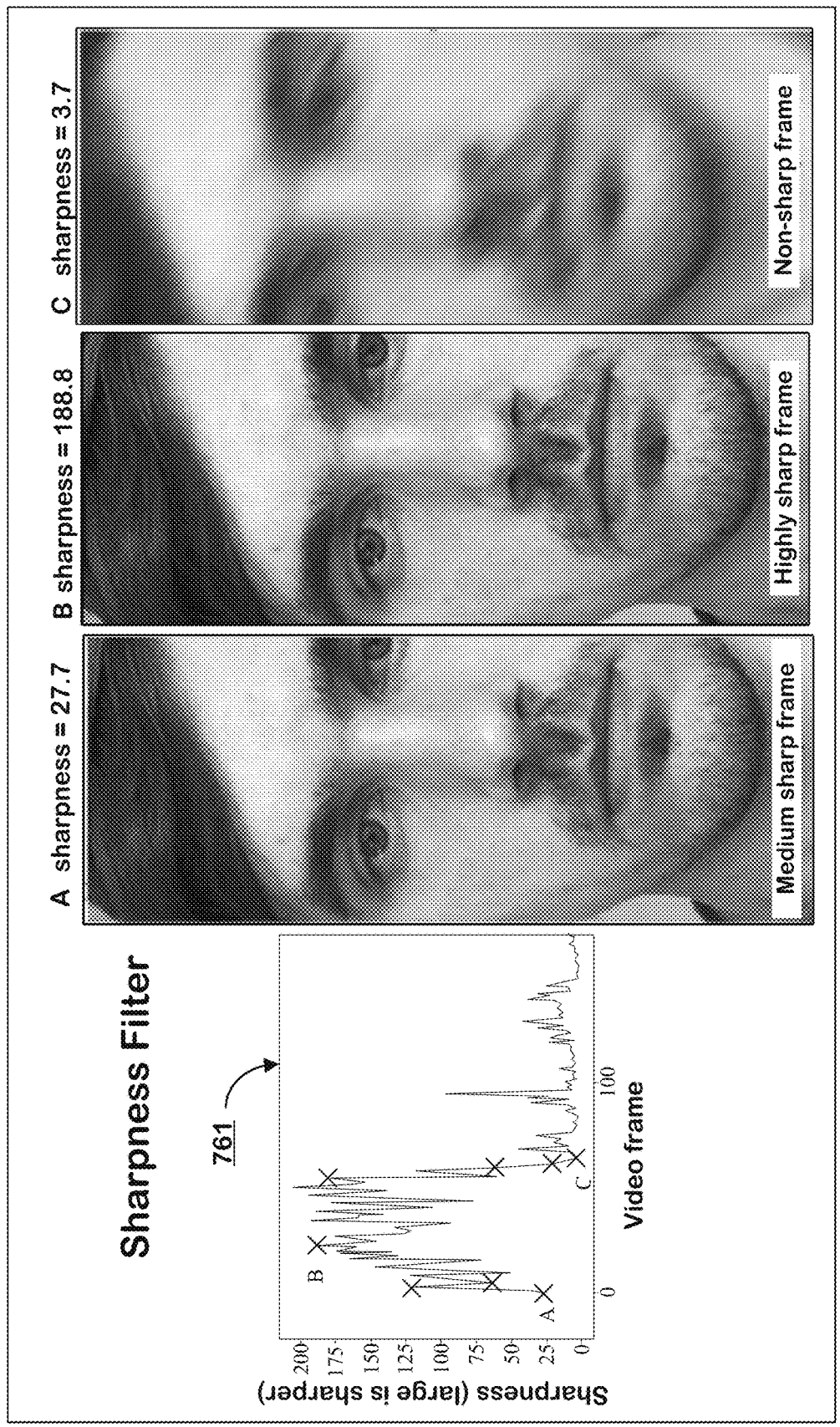
FIG. 7D presents an example of pre-processing including selection of a highly sharp image from a sequence of video frames.

FIGS. 7C and 7D present examples of image pre-processing that can be applied to face images of the users. The biometric data pre-processing engine 131 can include the logic to implement these pre-processing techniques. The following techniques are presented as examples, other pre-processing techniques can be implemented by the technology disclosed.

FIG. 7C illustrates examples of image pre-processing techniques that can be applied to face images. The technology disclosed can apply face detection (751) to ensure that facial data is used to generate registration and authentication features. Face segmentation can be applied to crop foreground face images and potentially noisy backgrounds can be removed. Illustration 755 shows segmentation of a foreground face image. The foreground facial image 757 is cropped and used for generating registration and authentication features. Pre-trained machine learning models such as convolutional neural networks (CNNs) can be applied to detect foreground from background as well as facial landmarks.

FIG. 7D presents an example data filter that can be applied to biometric input data to ensure good quality biometric input is used to generate registration and authentication features. The system can select multiple frames from a video of the user. Image frames that are sharpest are selected; blurry or unclear images are discarded. Graph 761 shows sharpness values for images from a video. The higher the value along the y-axis, the sharper the image. Three image frames A, B, and C are shown in FIG. 7D with different sharpness values for illustration purposes. Image B (in the middle) has a sharpness value of 188.8 which indicates that this is a highly sharp image frame. The sharpness value for image A (on the left) is 27.7 which indicates that this image frame has medium sharpness. A third image C (on the right) has a sharpness value of 3.7 which indicates that this is a blurry image. The system can use a 3×3 convolutional sharpness filter to select the sharpest image frames from a video of the user. From the three image frames shown in FIG. 7D, the system can select the sharpest image frame B and discard image frames A and C for input to the machine learning model. The system can select a plurality of images from the video with high sharpness values.

We now present alternative techniques that can be used to match the authentication feature vector (or login embedding) to the characteristic feature vector (or base embedding) for authenticating the worker during login to the trustworthy app running on the worker's device. The alternative techniques include a binning technique and a locality-preserving hashing technique to generate deterministic outputs from non-deterministic biometric inputs used during registration and login to the app.

Binning Technique for Authentication

Figure 8A:
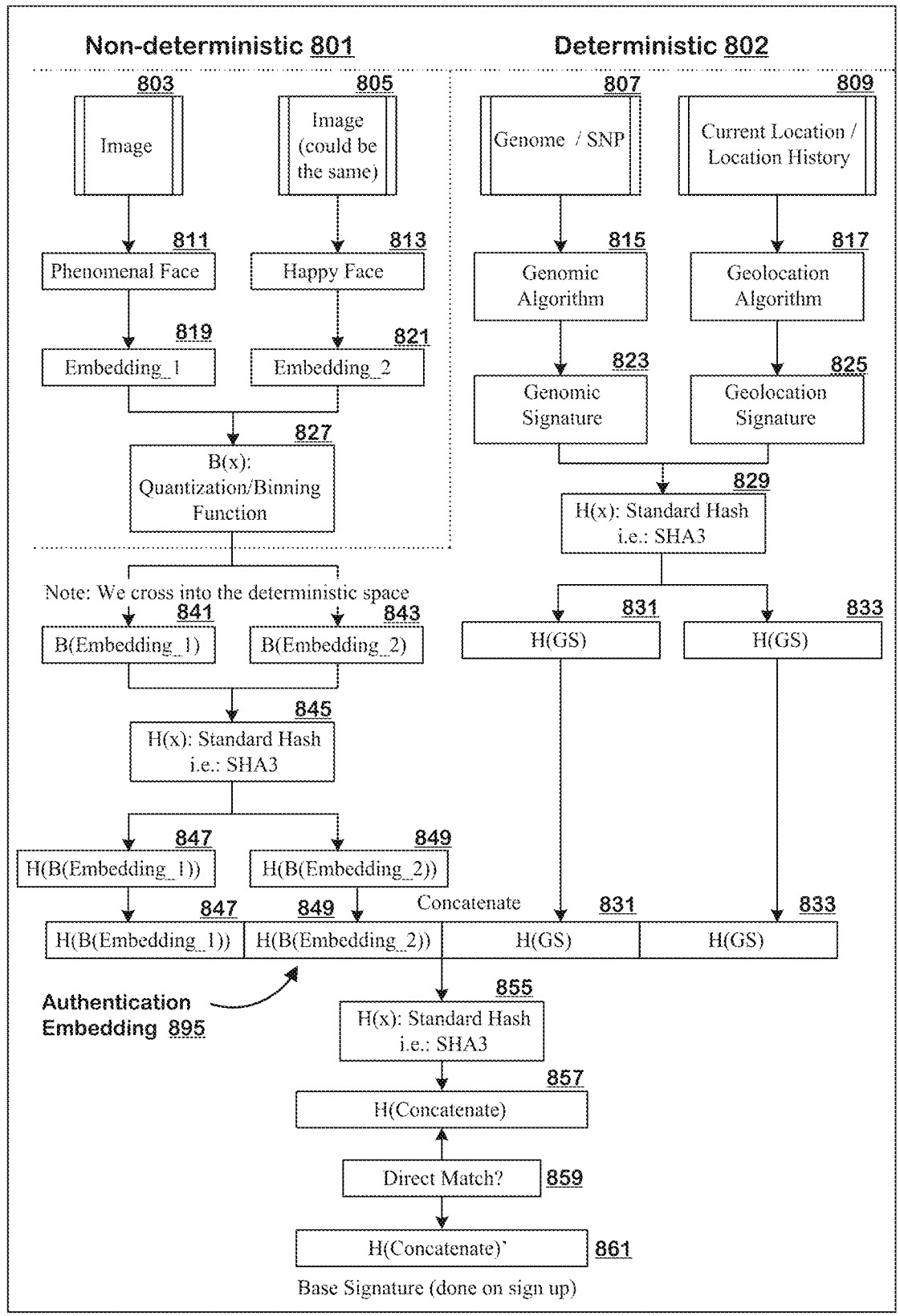
FIG. 8A presents a process flowchart for an implementation in which a binning function is used to quantize characteristic and authentication feature vectors for authenticating a user.

In an alternative implementation, the technology disclosed can apply a binning technique to authenticate users during authentication and match the authentication (or login) embedding to the registration embedding. FIG. 8A presents an example flow chart illustrating the binning technique to authenticate the user. Two types of inputs can be used to authenticate the user. Non-deterministic inputs 801 (listed on the left part of the flow chart) can include facial images, sound samples, etc. In this flow chart two facial images (same images or different images of the same user) can be provided as inputs to two different trained machine learning models. For example, a first image 803 can be processed by a trained Phenomenal Face model 811 and a second facial image 805 can be processed by a trained Happy Face model 813. The details of the Phenomenal Face model are presented in U.S. patent application Ser. No. 15/946,629, entitled "IMAGE-BASED SYSTEM AND METHOD FOR PREDICTING PHYSIOLOGICAL PARAMETERS," filed on Apr. 5, 2018 which is incorporated by reference as if fully set forth herein. The Happy Face model can have slightly different architecture than the Phenomenal Face model. The Happy Face machine learning model can be trained to classify moods of the user (e.g., 'UPSET', 'CALM', 'HAPPY', 'SAD', 'SURPRISED_V2', 'UNKNOWN') while the Phenomenal Face model outputs gender and estimates height, weight and age of the user when processing the facial images. Thus, two models can provide diverse embeddings (819 and 821) for the same user. Other examples of trained machine learning models that can be used to generate embeddings from facial images include MobileNet V2 model, ArcFace model, etc.

Figure 8B:
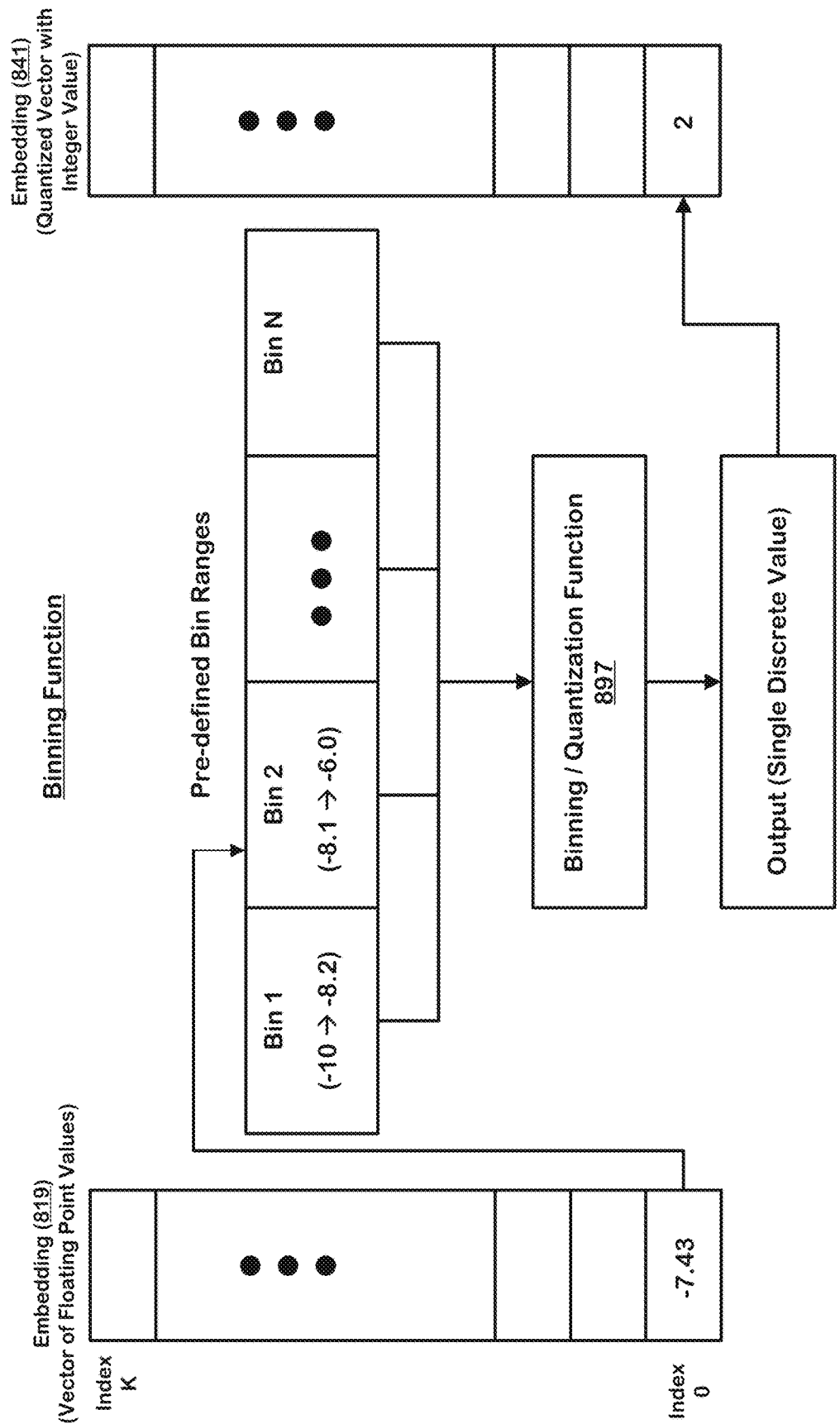
FIG. 8B presents an example binning function that can be used with the authentication example presented in FIG. 8A.

A binning or quantization function "B(x)" 827 can be applied to embedding_1 (819) and embedding_2 (821). We present an example binning function in FIG. 8B to illustrate quantization of an embedding, say 819. The embedding 819 can include floating point values at each index 0 to K. An example value −7.43 is shown at index 0 in embedding 819 in FIG. 8B. A binning function can include a pre-determined "N" number of bins. Each bin maps a range of floating-point values to an integer value. For example, floating point values between the range of −10 to −8.2 are mapped to bin 1, floating point values between the range of −8.1 to −6.0 are mapped to bin 2, and so on. Note, that the floating-point values can range from negative infinity to positive infinity for each element of the embedding 819. The binning function maps each bin to a discrete or integer value. In one example, the binning function assigns a bin number to the floating-point value. For example, the value −7.43 at index 0 of embedding 819 is mapped to bin 2 as it falls in the range −8.1 to −6.0. The output from the binning function 897 is then stored at respective index position in the quantized embedding 841. In one instance, the binning function can assign the bin number or another integer number to the mapped value. In this example, the bin number "2" is output by the binning function and stored in the index 0 location of the quantized embedding.

Referring back to FIG. 8A, the non-deterministic inputs are converted to deterministic outputs after the binning function is applied. The system applies a standard hash (e.g., SHA3) at step 845 to quantized embeddings 841 and 843, resulting in hashes H(B(Embedding_1)) 847 and H(B(Embedding_2)) 849.

The system can also include deterministic inputs 802 for authenticating the user. Examples of deterministic inputs include location history of the user or genomic data of the user. The system can extract a genomic signature (823) from the user's genomic data (807) by analyzing specific patterns and substrings of the sequencing data and/or SNPs (815). The current location or location history of the user (809) can also be used to generate a geolocation signature 825 by applying a geolocation algorithm 817. The geolocation algorithm can use the current location or location history of the user to generate latitude and longitude values that can used as a geolocation signature. The genomic and location inputs are deterministic i.e., the same output is obtained for given input values. The system can apply a standard hash (829) to genomic and geolocation signatures to generate hash values 831 and 833 respectively.

An authentication feature vector 895 (or authentication embedding) is generated by combining the embedding 847, 849 and hashes 831 and 833. A hash 857 of the authentication embedding is generated using a standard hashing algorithm such as SHA3 or Secure Hash Algorithm 3 (855). The hash 857 is matched to a hash 861 generated by a hashing registration feature vector or registration embedding that is previously generated during the registration process of the user. If the hash values for the authentication feature vector and the registration feature vector match (859), the user is authenticated. The registration feature vector can be generated using the same process as presented in FIGS. 8A and 8B.

Locality Preserving Hashing Technique for Authentication

In another implementation, the technology disclosed can apply a locality-preserving hash to authenticate users when non-deterministic biometric inputs are used to generate registration and authentication feature vectors. A locality preserving hash (LPH) is a hash function that maps a point or points in a multi-dimensional space to a scalar value such that the relative distance between input values is preserved in the relative distance between the output hash values. Input values that are closer to each other will produce output hash values that are closer to each other.

Figure 9:
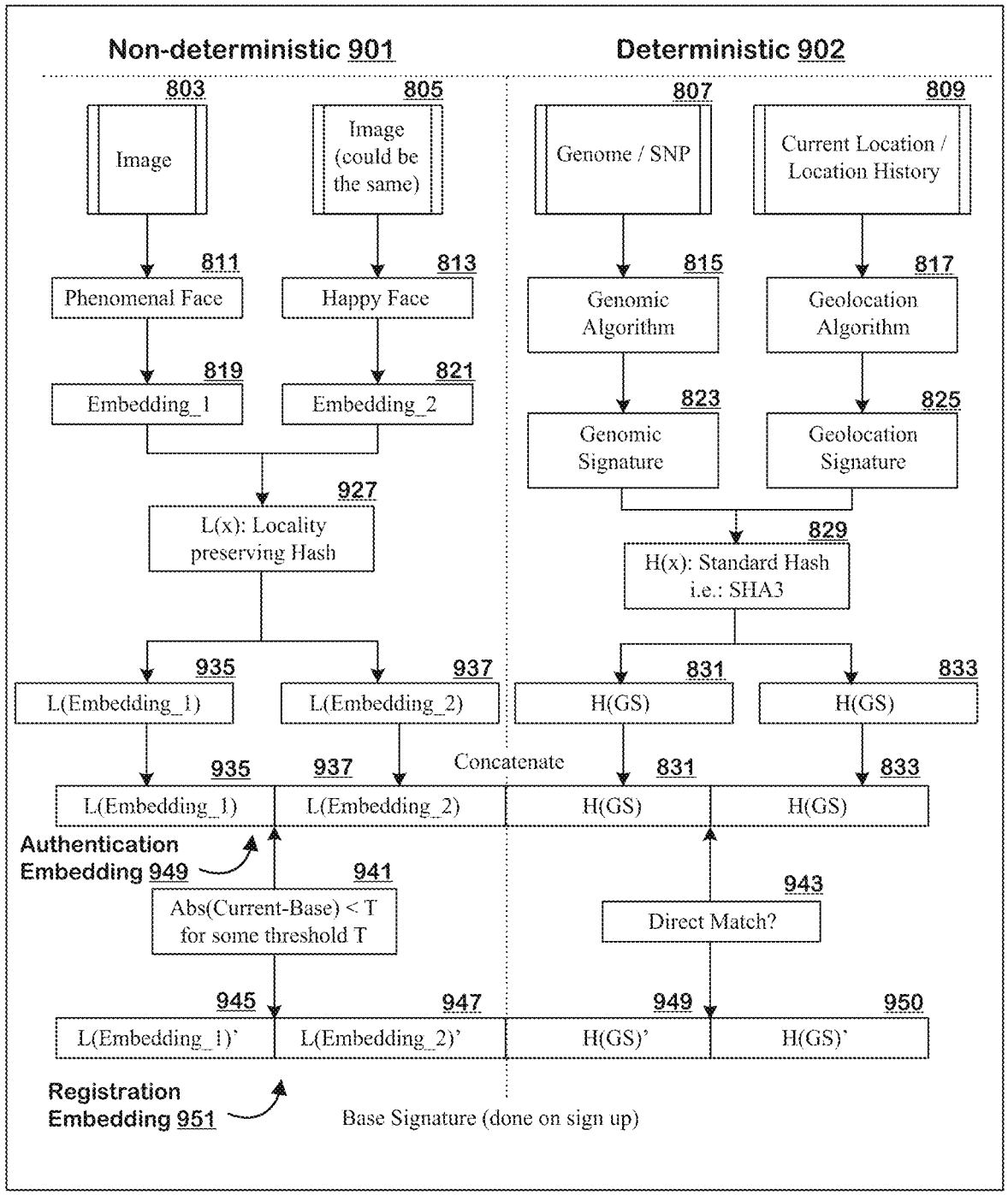
FIG. 9 presents a process flowchart for an implementation in which a locality preserving hashing is used to calculate hashes of characteristic and authentication feature vectors for authenticating a user.

FIG. 9 presents a flowchart for authenticating a user when locality-preserving hashing is applied to embeddings or feature vectors generated from non-deterministic biometric inputs 901. The system can also include deterministic inputs 902. The process to generate embeddings 819 and 821 is similar to the process described in FIG. 8A. Similarly, the processing steps for deterministic inputs are similar to the ones presented in FIG. 8A. A locality-preserving hash is applied to embeddings 819 and 821 to generate hashes L(Embedding_1) 935 and L(Embedding_2) 937 respectively (step 927). Authentication embedding can be generated by concatenating the hashes 935 and 937 with hashes 831 and 833 from deterministic inputs. The respective hash values in the authentication embedding 949 and the registration embedding 951 are compared. The registration embedding can comprise of embeddings 945 and 947 generated from non-deterministic inputs and hashes 949 and 950 calculated from deterministic inputs. For example, for the hash values generated using locality preserving hashing, a difference between the registration (or base) and the authentication (or current) hash values is compared to a threshold (941). If the difference is less than the threshold then it means the outputs are positioned close to each other and likely represent the same user. The hash values for the deterministic part can be matched directly between the authentication and registration embeddings to authenticate the user. The registration embedding 951 represents the base embedding generated during the registration process.

Particular Implementations

The technology disclosed is related to the registration, authentication and verification of authenticated users using non-deterministic biometric inputs.

The technology disclosed can be practiced as a system, method, device, product, computer readable media, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Registration (Cosine Distance, LPH, Binning)

The technology disclosed can be practiced as a method of establishing authentication credentials using a plurality of non-deterministic registration biometric inputs. The method includes feeding, during registration, a plurality of non-deterministic biometric inputs to a trained machine learning model and generating sets of feature vectors. The non-deterministic biometric inputs can include a plurality of face images and a plurality of voice samples of a user. The method includes projecting the sets of feature vectors onto the surface of a hyper-sphere. The method includes computing a characteristic identity vector representing the user based on a user's set of the projected feature vectors. The characteristic identity vector is also referred to as a base embedding or a characteristic feature vector. The method includes saving the characteristic identity vector for use during the authentication of the user.

This method and other implementations of the technology disclosed can include one or more of the following features. In the interest of conciseness, the combinations of features disclosed in this application are not individually enumerated and are not repeated with each base set of features. Features applicable to methods, systems, and articles of manufacture are not repeated for each statutory class set of base features. The reader will understand how features identified in this section can readily be combined with base features in other statutory classes.

In one implementation, the method includes registering a cryptographic signature of the characteristic identity vector with an identity server. The cryptographic signature can be accompanied by a photograph of the user selected from the plurality of face images.

In one implementation, the method includes registering the characteristic identity vector with an identity server. The characteristic identity vector can be accompanied by a photograph of the user that becomes one of the plurality of face images used to compute the characteristic identity vector.

The set of features can be projected onto the surface of a unit hyper-sphere.

In one implementation, the method includes registering the characteristic identity vector with an identity server. The characteristic identity vector can be accompanied by a photograph of the user that produces feature vectors that are within a predetermined distance of the projection of the feature vectors for the plurality of face images onto the surface of the hyper-sphere.

In one implementation, the method includes using one or more deterministic inputs to establish the authentication credentials by feeding genomic data to a hash. The method includes using the hashed genomic data as at least one dimension of the characteristic identity vector.

In one implementation, the method includes preprocessing the face image data to separate the face from the background before generating the feature vectors.

In one implementation, the method includes preprocessing the face image data by selecting individual frames from a video sequence. The individual frames can be selected based on an image sharpness metric.

In one implementation, the method includes preprocessing the voice data by selecting an audio segment corresponding to a phrase specified for the user to read.

A second method implementation of the technology disclosed can be used to establish authentication credentials using a plurality of non-deterministic registration biometric inputs. The method includes feeding, during registration, a plurality of non-deterministic biometric inputs to a plurality of trained machine learning models. The method includes generating a plurality of feature vectors from the respective trained machine learning models. The non-deterministic biometric inputs can include an image of a user and/or a voice sample of the user. The method includes applying a distance preserving hash to the plurality of feature vectors to generate a registration hash representing the user. The method includes saving the registration hash for use during the authentication of the user.

A third method implementation of the technology disclosed can be used to establish authentication credentials using a plurality of non-deterministic registration biometric inputs. The method includes feeding, during registration, a plurality of non-deterministic biometric inputs to a plurality of trained machine learning models and generating a plurality of feature vectors from the respective trained machine learning models. The non-deterministic biometric inputs can include an image of a user and/or a voice sample of the user. The method includes applying a binning function to non-integer values in the plurality of feature vectors to quantize the non-integer values to integer values. The binning function can map a range of non-integer values to an integer value. The method includes applying a hash function to the plurality of quantized feature vectors to generate a registration hash. The method includes saving the registration hash for use during the authentication of the user.

Other implementations consistent with the methods may include a non-transitory computer readable storage medium storing instructions executable by a processor to perform any of the methods described above. Yet another implementation may include a system with memory loaded from a computer readable storage medium with program instructions to perform any of the methods described above. The system can be loaded from either a transitory or a non-transitory computer readable storage medium.

Aspects of the technology disclosed can be practiced as a system that includes one or more processors coupled to memory. The memory is loaded with computer instructions to establish authentication credentials using a plurality of non-deterministic registration biometric inputs. The system includes logic to feed, during registration, a plurality of non-deterministic biometric inputs to a trained machine learning model and generate sets of feature vectors. The non-deterministic biometric inputs can include a plurality of face images and a plurality of voice samples of a user. The system includes logic to project the sets of feature vectors onto the surface of a hyper-sphere. The system includes logic to compute a characteristic identity vector representing the user based on a user's set of the projected feature vectors. The system includes logic to save the characteristic identity vector for use during the authentication of the user.

A second system implementation of the technology includes one or more processors coupled to memory. The memory is loaded with computer instructions to establish authentication credentials using a plurality of non-deterministic registration biometric inputs. The system includes logic to feed, during registration, the plurality of non-deterministic biometric inputs to a plurality of trained machine learning models and generate a plurality of feature vectors from the respective trained machine learning models. The non-deterministic biometric inputs can include an image of a user and/or a voice sample of a user. The system includes logic to apply a distance-preserving (or a locality-preserving) hash to the plurality of feature vectors to generate a registration hash representing the user. The system includes logic to save the registration hash for use during the authentication of the user.

A third system implementation of the technology includes one or more processors coupled to memory. The memory is loaded with computer instructions to establish authentication credentials using a plurality of non-deterministic registration biometric inputs. The system includes logic to feed, during registration, a plurality of non-deterministic biometric inputs to a plurality of trained machine learning models and generate a plurality of feature vectors from the respective trained machine learning models. The non-deterministic biometric inputs can include an image of a user and/or a voice sample of the user. The system includes logic to apply a binning function to non-integer values in the plurality of feature vectors to quantize the non-integer values to integer values. The binning function maps a range of non-integer values to an integer value. The system includes logic to apply a hash function to the plurality of quantized feature vectors to generate a registration hash. The system includes logic to save the registration hash for use during the authentication of the user.

The computer-implemented systems can incorporate any of the features of the method described immediately above or throughout this application that apply to the method implemented by the system. In the interest of conciseness, alternative combinations of system features are not individually enumerated. Features applicable to systems, methods, and articles of manufacture are not repeated for each statutory class set of base features. The reader will understand how features identified in this section for one statutory class can readily be combined with base features in other statutory classes.

Other implementations may include a non-transitory computer readable storage medium storing instructions executable by a processor to perform functions of the system described above. Yet another implementation may include a method performing the functions of the system described above.

As an article of manufacture, rather than a method, a non-transitory computer readable medium (CRM) can be loaded with program instructions executable by a processor. The program instructions when executed, implement the computer-implemented method described above. Alternatively, the program instructions can be loaded on a non-transitory CRM and, when combined with appropriate hardware, become a component of one or more of the computer-implemented systems that practice the method disclosed.

Each of the features discussed in this particular implementation section for the method implementation apply equally to CRM implementation. As indicated above, all of the method features are not repeated here, in the interest of conciseness, and should be considered repeated by reference.

Authentication (Cosine Distance, LPH, Binning)

The technology disclosed can be practiced as a method of authentication using a plurality of non-deterministic authentication biometric inputs. The method includes receiving a plurality of non-deterministic biometric inputs with a request for authentication. The method includes feeding the non-deterministic biometric inputs to a trained machine learning model and generating a set of authentication feature vectors. The non-deterministic authentication biometric input can include an image and a voice sample of a user. The method includes projecting the set of feature vectors onto the surface of a hyper-sphere. The method includes authenticating the user when a cosine distance between the authentication feature vector and a characteristic identity vector previously registered for the user is less than a pre-determined threshold.

This method and other implementations of the technology disclosed can include one or more of the following features. In the interest of conciseness, the combinations of features disclosed in this application are not individually enumerated and are not repeated with each base set of features. Features applicable to methods, systems, and articles of manufacture are not repeated for each statutory class set of base features. The reader will understand how features identified in this section can readily be combined with base features in other statutory classes.

The sets of feature vectors can be projected onto the surface of a unit hyper-sphere.

The characteristic identity vector for the user was determined by averaging feature vectors for a plurality of images and for a plurality of voice samples on a user-by-user basis.

The predetermined threshold was determined from variance among projected feature vectors from the plurality of images and the plurality of voice samples on a user-by-user basis.

The predetermined threshold was determined from variance among projected feature vectors from the plurality of images and the plurality of voice samples for classes of users.

The predetermined threshold was determined from variance among projected feature vectors from the plurality of images and the plurality of voice samples across users.

A second method implementation of the technology disclosed can be used to authenticate a user using a plurality of non-deterministic authentication biometric inputs. The method includes receiving a plurality of non-deterministic authentication biometric inputs with a request for authentication. The method includes feeding the non-deterministic authentication biometric inputs to a plurality of trained machine learning models and generating a plurality of authentication feature vectors. The non-deterministic authentication biometric input can include an image and a voice sample of a user. The method includes applying a distance-preserving hash to the plurality of authentication feature vectors to generate an authentication hash representing the user. The method includes authenticating the user when a difference between the authentication hash and a registration hash previously registered for the user is less than a pre-determined threshold.

A third method implementation of the technology disclosed can be used to authenticate a user using a plurality of non-deterministic authentication biometric inputs. The method includes receiving the plurality of non-deterministic authentication biometric inputs with a request for authentication. The method includes feeding the non-deterministic authentication biometric inputs to a plurality of trained machine learning models and generating a plurality of authentication feature vectors. The non-deterministic authentication biometric input includes an image and a voice sample of a user. The method includes applying a binning function to non-integer values in the plurality of authentication feature vectors to quantize the non-integer values to integer values. The method includes applying a hash function to the plurality of quantized authentication feature vectors to generate an authentication hash. The method includes authenticating the user when the authentication hash matches a registration hash previously registered for the user.

Other implementations consistent with the methods may include a non-transitory computer readable storage medium storing instructions executable by a processor to perform any of the methods described above. Yet another implementation may include a system with memory loaded from a computer readable storage medium with program instructions to perform any of the methods described above. The system can be loaded from either a transitory or a non-transitory computer readable storage medium.

Aspects of the technology disclosed can be practiced as a system that includes one or more processors coupled to memory. The memory is loaded with computer instructions to authenticate a user using a plurality of non-deterministic authentication biometric inputs. The system includes logic to receive a plurality of non-deterministic biometric inputs with a request for authentication. The system includes logic to feed the non-deterministic biometric inputs to a trained machine learning model and generate a set of authentication feature vectors. The non-deterministic authentication biometric input can include an image and a voice sample of a user. The system includes logic to project the set of feature vectors onto the surface of a hyper-sphere. The system includes logic to authenticate the user when a cosine distance between the authentication feature vector and a characteristic identity vector previously registered for the user is less than a pre-determined threshold.

A second system implementation of the technology includes one or more processors coupled to memory. The memory is loaded with computer instructions to authenticate a user using a plurality of non-deterministic authentication biometric inputs. The system includes logic to receive a plurality of non-deterministic authentication biometric inputs with a request for authentication. The system includes logic to feed the non-deterministic authentication biometric inputs to a plurality of trained machine learning models and generate a plurality of authentication feature vectors. The non-deterministic authentication biometric input can include an image and a voice sample of a user. The system includes logic to apply a distance-preserving hash to the plurality of authentication feature vectors to generate an authentication hash representing the user. The system includes logic to authenticate the user when a difference between the authentication hash and a registration hash previously registered for the user is less than a pre-determined threshold.

A third system implementation of the technology includes one or more processors coupled to memory. The memory is loaded with computer instructions to authenticate a user using a plurality of non-deterministic authentication biometric inputs. The system includes logic to receive a plurality of non-deterministic authentication biometric inputs with a request for authentication. The system includes logic to feed the non-deterministic authentication biometric inputs to a plurality of trained machine learning models and generate a plurality of authentication feature vectors. The non-deterministic authentication biometric input can include an image and/or a voice sample of a user. The system includes logic to apply a binning function to non-integer values in the plurality of authentication feature vectors to quantize the non-integer values to integer values. The system includes logic to apply a hash function to the plurality of quantized authentication feature vectors to generate an authentication hash. The system includes logic to authenticate the user when the authentication hash matches a registration hash previously registered for the user.

The computer implemented systems can incorporate any of the features of the method described immediately above or throughout this application that apply to the method implemented by the system. In the interest of conciseness, alternative combinations of system features are not individually enumerated. Features applicable to systems, methods, and articles of manufacture are not repeated for each statutory class set of base features. The reader will understand how features identified in this section for one statutory class can readily be combined with base features in other statutory classes.

Other implementations may include a non-transitory computer readable storage medium storing instructions executable by a processor to perform functions of the system described above. Yet another implementation may include a method performing the functions of the system described above.

As an article of manufacture, rather than a method, a non-transitory computer readable medium (CRM) can be loaded with program instructions executable by a processor. The program instructions when executed, implement the computer-implemented method described above. Alternatively, the program instructions can be loaded on a non-transitory CRM and, when combined with appropriate hardware, become a component of one or more of the computer-implemented systems that practice the method disclosed.

Each of the features discussed in this particular implementation section for the method implementation apply equally to CRM implementation. As indicated above, all the method features are not repeated here, in the interest of conciseness, and should be considered repeated by reference.

Verification (Scannable Code Generation)

The technology disclosed can be practiced as a method of generating a scannable code for an authenticated user. The method includes securely sending from an authenticated user's device, a unique identifier for the authenticated user, a cryptographic signature for the authenticated user, and a timestamp to a registration server. The authenticated user's device (client) receives a success nonce from the registration server. The success nonce can be used by the registration server to access a user's photo identifier and access a hash of at least the signature of the authenticated user. The authenticated user's device recreates the hash of at least the signature stored by the registration server. The user's device can generate a scannable code including an encrypted success nonce and the recreated hash. The user's device can produce the scannable code from the results of the encrypted success nonce and the recreated hash. The scannable code can be displayed for a validator to scan to verify that a return-to-work request is from the authenticated user.

This method and other implementations of the technology disclosed can include one or more of the following features. In the interest of conciseness, the combinations of features disclosed in this application are not individually enumerated and are not repeated with each base set of features. Features applicable to methods, systems, and articles of manufacture are not repeated for each statutory class set of base features. The reader will understand how features identified in this section can readily be combined with base features in other statutory classes.

In one implementation, the method includes receiving a shared encryption key and a public encryption key.

The cryptographic signature for the authenticated user can be generated by applying a shared encryption key to a biometric identifier for the authenticated user.

In one implementation, the method includes sending the signature for the unique identifier for the authenticated user to the registration server for validation.

In one implementation, the method includes generating the hash of at least the signature and the shared key.

In one implementation, the method includes sending the timestamp to the registration server for validation. Upon validation, the registration server can generate a success nonce and a hash of at least the signature. The registration server can then store the nonce, the hash and a photo ID for the authenticated user to a database. At least one or more of the data in the triplet of the nonce, the hash and the photo ID can be encrypted at rest.

In one implementation, the authenticated user's device (or client device) can recreate the hash of the shared key stored by the registration server and the signature.

In one implementation, the authenticated user's device can encrypt the success nonce and the recreated hash with the public encryption key of the registration server.

In one implementation, the authenticated user's device can display a user photograph for the validator to verify that a return-to-work request is from the authenticated user.

The biometric identifier of the authenticated user can be generated by feeding a plurality of non-deterministic biometric inputs to a trained machine learning model to produce a plurality of feature vectors. The plurality of feature vectors can be projected onto the surface of a unit hyper-sphere. A characteristic identity vector is computed representing the user based on the user's projected feature vectors. The non-deterministic biometric inputs can include a plurality of face images and a plurality of voice samples of a user.

The success nonce can be a one-time use code for use with the scannable code. The use of one-time nonce codes can reduce the likelihood of replays of messages by an unauthenticated client to present itself as the authenticated user.

A second method implementation of the technology disclosed can include verifying a request by a registration server. The method includes securely receiving a nonce code from a validator that has scanned a scannable code. The nonce code is previously generated by the registration server. The data in the secured message can also include a recreated hash, previously associated by the registration server with the nonce. The method includes extracting the nonce code and the recreated hash from the scannable code. The method includes using the nonce code to access a hash of the record and photo ID of an authenticated user. The method includes validating the recreated hash against a hash of record. The method includes marking the nonce code as used. The method includes sending the validator, a photo of the authenticated user and a success message.

This method and other implementations of the technology disclosed can include one or more of the following features. In the interest of conciseness, the combinations of features disclosed in this application are not individually enumerated and are not repeated with each base set of features. Features applicable to methods, systems, and articles of manufacture are not repeated for each statutory class set of base features. The reader will understand how features identified in this section can readily be combined with base features in other statutory classes.

The recreated hash can be generated using at least a signature for the authenticated user.

In one implementation, the method includes decrypting the success code with a private key of the registration server.

Other implementations consistent with methods may include a non-transitory computer readable storage medium storing instructions executable by a processor to perform any of the methods described above. Yet another implementation may include a system with memory loaded from a computer readable storage medium with program instructions to perform any of the methods described above. The system can be loaded from either a transitory or a non-transitory computer readable storage medium.

Aspects of the technology disclosed can be practiced as a system that includes one or more processors coupled to memory. The memory is loaded with computer instructions to generate a scannable code for an authenticated user. The system includes logic to securely send from an authenticated user's device, a unique identifier for the authenticated user, a cryptographic signature for the authenticated user, and a timestamp to a registration server. The authenticated user's device (client) receives a success nonce from the registration server. The success nonce can be used by the registration server to access a user's photo identifier and access a hash of at least the signature of the authenticated user. The authenticated user's device can recreate the hash of at least the signature stored by the registration server. The user's device can generate a scannable code including the encrypted success nonce and the recreated hash. The user's device can produce the scannable code from the results of the encrypted success nonce and the recreated hash. The scannable code can be displayed for a validator to scan to verify that a return-to-work request is from the authenticated user.

A second system implementation of the technology includes one or more processors coupled to memory. The memory is loaded with computer instructions to securely receive a nonce code from a validator that has scanned a scannable code. The nonce code is previously generated by the registration server. The data in the secured message can also include a recreated hash, previously associated by the registration server with the nonce. The system includes logic to extract the nonce code and the recreated hash from the scannable code. The system includes logic to use the nonce code to access a hash of record and photo ID of an authenticated user. The system includes logic to validate the recreated hash against a hash of record. The system includes logic to mark the nonce code as used. The system includes logic to send the validator, a photo of the authenticated user and a success message.

The computer implemented systems can incorporate any of the features of the method described immediately above or throughout this application that apply to the method implemented by the system. In the interest of conciseness, alternative combinations of system features are not individually enumerated. Features applicable to systems, methods, and articles of manufacture are not repeated for each statutory class set of base features. The reader will understand how features identified in this section for one statutory class can readily be combined with base features in other statutory classes.

Other implementations may include a non-transitory computer readable storage medium storing instructions executable by a processor to perform functions of the system described above. Yet another implementation may include a method performing the functions of the system described above.

As an article of manufacture, rather than a method, a non-transitory computer readable medium (CRM) can be loaded with program instructions executable by a processor. The program instructions when executed, implement the computer-implemented method described above. Alternatively, the program instructions can be loaded on a non-transitory CRM and, when combined with appropriate hardware, become a component of one or more of the computer-implemented systems that practice the method disclosed.

Each of the features discussed in this particular implementation section for the method implementation apply equally to CRM implementation. As indicated above, all the method features are not repeated here, in the interest of conciseness, and should be considered repeated by reference.

CLAUSES

Scannable Code Generation—(Authenticated User Side)
1. A computer-implemented method of generating a scannable code for an authenticated user, the method including:
securely sending, to a registration server, a unique identifier for the authenticated user, a cryptographic signature for the authenticated user, and a timestamp;
receiving, from the registration server, a success nonce, usable by the registration server to access a user photo identifier and access a hash of at least the signature;
recreating the hash of the of at least the signature stored by the registration server;

generating a scannable code including encrypting the success nonce and the recreated hash and producing the scannable code from results of the encrypting; and displaying the scannable code for a validator to scan for verifying that a return-to-work request is from the authenticated user.

2. The method of clause 1, further including:

receiving a shared encryption key and a public encryption key.

3. The method of clause 2, wherein the cryptographic signature for the authenticated user is generated by applying a shared encryption key to a biometric identifier for the authenticated user.

4. The method of clause 3, further including:

sending to the registration server, for validating, signature for the unique identifier for the authenticated user.

5. The method of clause 3, further including:

generating the hash of at least the signature and the shared key.

6. The method of clause 1, further including:

sending to the registration server, for validating, the timestamp, then generating a success nonce and a hash of at least the signature, then storing the nonce, the hash and a photo ID for the authenticated user.

7. The method of clause 1, recreating the hash further including:

a shared key stored by the registration server.

8. The method of clause 2, further including:

encrypting the success nonce and the recreated hash with the public encryption key of the registration server.

9. The method of clause 3, wherein the biometric identifier of the authenticated user was generated by feeding a plurality of non-deterministic biometric inputs to a trained machine learning model producing a plurality of feature vectors, projecting the plurality of feature vectors onto a surface of a unit hyper-sphere and computing a characteristic identity vector representing the user based on the user's projected feature vectors.

10. The method of clause 9, wherein the non-deterministic biometric inputs include a plurality of face images and a plurality of voice samples of a user.

11. The method of clause 1, wherein the success nonce is a one-time use code for use with the scannable code.

Scannable Code Scanning—(Registration Server Side)

12. A computer-implemented method of verifying a request by a registration server, the method including:

securely receiving, from a validator that has scanned a scannable code that encodes a nonce code, previously generated by the registration server, and a recreated hash, previously associated by the registration server with the nonce;

extracting the nonce code and the recreated hash from the scannable code;

using the nonce code to access a hash of record and photo ID of an authenticated user;

validating the recreated hash against a hash of record;

marking the nonce code as used; and sending the validator, a photo of the authenticated user and a success message.

13. The method of clause 12, wherein the recreated hash is generated using at least a signature for the authenticated user.

14. The method of clause 12, further including:

decrypting the success code with a private key of the registration server.

15. A system including one or more processors coupled to memory, the memory loaded with computer instructions to generate a scannable code for an authenticated user, the instructions, when executed on the processors, implement actions comprising:

securely sending, to a registration server, a unique identifier for the authenticated user, a cryptographic signature for the authenticated user, and a timestamp;

receiving, from the registration server, a success nonce, usable by the registration server to access a user photo identifier and access a hash of at least the signature;

recreating the hash of the of at least the signature stored by the registration server;

generating a scannable code including encrypting the success nonce and the recreated hash and producing the scannable code from results of the encrypting; and displaying the scannable code for a validator to scan for verifying that a return-to-work request is from the authenticated user.

16. The system of clause 15, further implementing actions comprising:

receiving a shared encryption key and a public encryption key.

17. The system of clause 16, wherein the cryptographic signature for the authenticated user is generated by applying a shared encryption key to a biometric identifier for the authenticated user.

18. The system of clause 17, further implementing actions comprising:

sending to the registration server, for validating, signature for the unique identifier for the authenticated user.

19. The system of clause 17, further implementing actions comprising:

generating the hash of at least the signature and the shared key.

20. The system of clause 15, further implementing actions comprising:

sending to the registration server, for validating, the timestamp, then generating a success nonce and a hash of at least the signature, then storing the nonce, the hash and a photo ID for the authenticated user.

21. The system of clause 15, wherein recreating the hash further including a shared key stored by the registration server.

22. The system of clause 16, further implementing actions comprising:

encrypting the success nonce and the recreated hash with the public encryption key of the registration server.

23. The system of clause 17, wherein the biometric identifier of the authenticated user was generated by feeding a plurality of non-deterministic biometric inputs to a trained machine learning model producing a plurality of feature vectors, projecting the plurality of feature vectors onto a surface of a unit hyper-sphere and computing a characteristic identity vector representing the user based on the user's projected feature vectors.

24. The system of clause 23, wherein the non-deterministic biometric inputs include a plurality of face images and a plurality of voice samples of a user.

25. The system of clause 15, wherein the success nonce is a one-time use code for use with the scannable code.

26. A system including one or more processors coupled to memory, the memory loaded with computer instructions to verify a request by a registration server, the instructions, when executed on the processors, implement actions comprising:

securely receiving, from a validator that has scanned a scannable code that encodes a nonce code, previously generated by the registration server, and a recreated hash, previously associated by the registration server with the nonce;

extracting the nonce code and the recreated hash from the scannable code;

using the nonce code to access a hash of record and photo ID of an authenticated user;

validating the recreated hash against a hash of record;

marking the nonce code as used; and sending the validator, a photo of the authenticated user and a success message.

27. The system of clause 26, wherein the recreated hash is generated using at least a signature for the authenticated user.

28. The system of clause 26, further implementing actions comprising:

decrypting the success code with a private key of the registration server.

29. A non-transitory computer readable storage medium impressed with computer program instructions to generate a scannable code for an authenticated user, the instructions, when executed on a processor, implement a method comprising:

securely sending, to a registration server, a unique identifier for the authenticated user, a cryptographic signature for the authenticated user, and a timestamp;

receiving, from the registration server, a success nonce, usable by the registration server to access a user photo identifier and access a hash of at least the signature;

recreating the hash of the of at least the signature stored by the registration server;

generating a scannable code including encrypting the success nonce and the recreated hash and producing the scannable code from results of the encrypting; and displaying the scannable code for a validator to scan for verifying that a return-to-work request is from the authenticated user.

30. The non-transitory computer readable storage medium of clause 29, implementing the method further comprising: receiving a shared encryption key and a public encryption key.

31. The non-transitory computer readable storage medium of clause 30, wherein the cryptographic signature for the authenticated user is generated by applying a shared encryption key to a biometric identifier for the authenticated user.

32. The non-transitory computer readable storage medium of clause 31, implementing the method further comprising: sending to the registration server, for validating, signature for the unique identifier for the authenticated user.

33. The non-transitory computer readable storage medium of clause 31, implementing the method further comprising: generating the hash of at least the signature and the shared key.

34. The non-transitory computer readable storage medium of clause 29, implementing the method further comprising: sending to the registration server, for validating, the timestamp, then generating a success nonce and a hash of at least the signature, then storing the nonce, the hash and a photo ID for the authenticated user.

35. The non-transitory computer readable storage medium of clause 29, wherein recreating the hash further including a shared key stored by the registration server.

36. The non-transitory computer readable storage medium of clause 30, implementing the method further comprising: encrypting the success nonce and the recreated hash with the public encryption key of the registration server.

37. The non-transitory computer readable storage medium of clause 31, wherein the biometric identifier of the authenticated user was generated by feeding a plurality of non-deterministic biometric inputs to a trained machine learning model producing a plurality of feature vectors, projecting the plurality of feature vectors onto a surface of a unit hyper-sphere and computing a characteristic identity vector representing the user based on the user's projected feature vectors.

38. The non-transitory computer readable storage medium of clause 37, wherein the non-deterministic biometric inputs include a plurality of face images and a plurality of voice samples of a user.

39. The non-transitory computer readable storage medium of clause 29, wherein the success nonce is a one-time use code for use with the scannable code.

40. A non-transitory computer readable storage medium impressed with computer program instructions to verify a request by a registration server, the instructions, when executed on a processor, implement a method comprising:

securely receiving, from a validator that has scanned a scannable code that encodes a nonce code, previously generated by the registration server, and a recreated hash, previously associated by the registration server with the nonce;

extracting the nonce code and the recreated hash from the scannable code;

using the nonce code to access a hash of record and photo ID of an authenticated user;

validating the recreated hash against a hash of record;

marking the nonce code as used; and sending the validator, a photo of the authenticated user and a success message.

41. The non-transitory computer readable storage medium of clause 40, wherein the recreated hash is generated using at least a signature for the authenticated user.

42. The non-transitory computer readable storage medium of clause 40, implementing the method further comprising: decrypting the success code with a private key of the registration server.

Computer System

Figure 10:
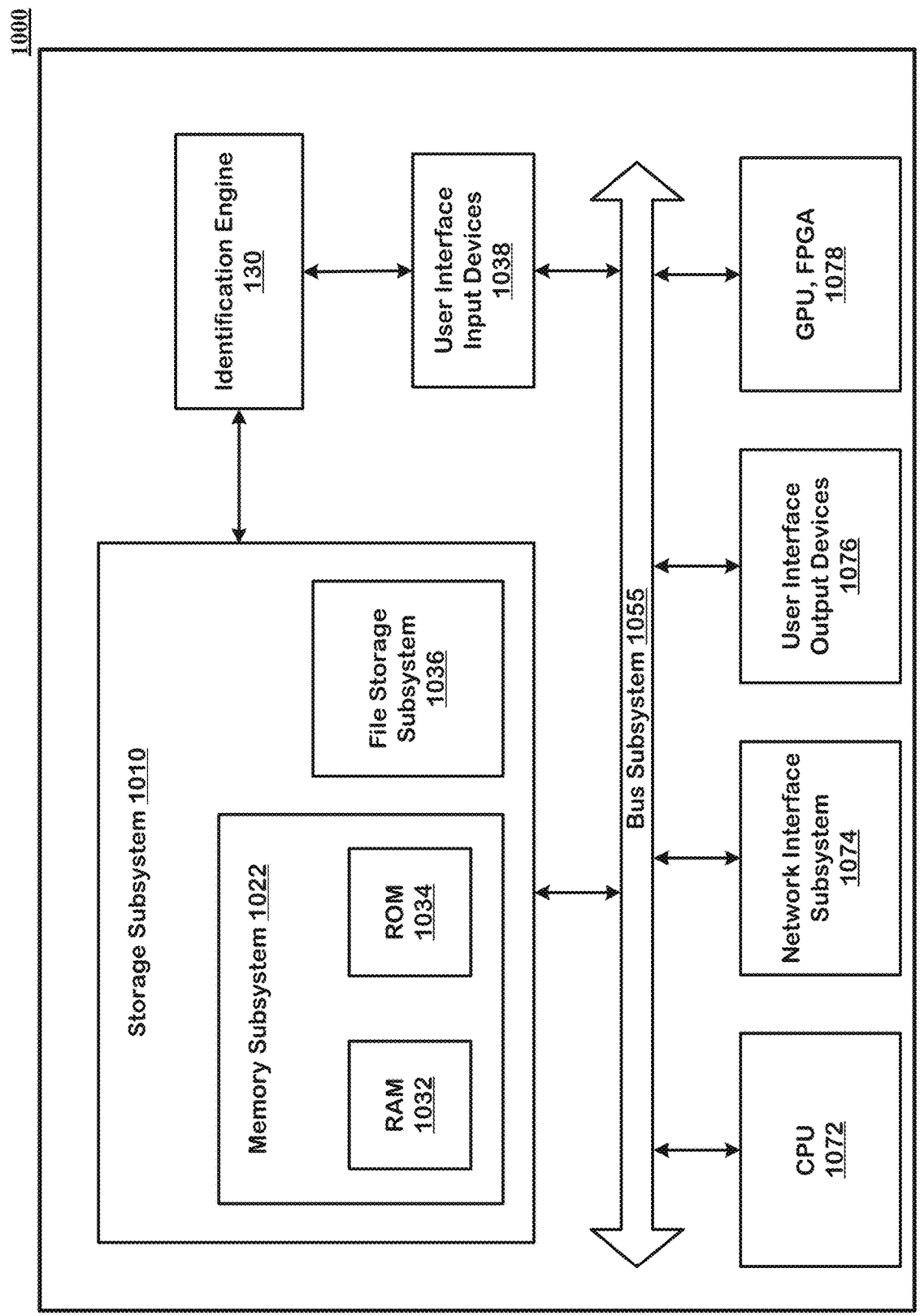
FIG. 10 is a simplified block diagram of a computer system that can be used to implement the technology disclosed.

A computer-implemented method implementation of the technology disclosed includes Computer System 1000 as shown in FIG. 10.

FIG. 10 is a simplified block diagram of a computer system 1000 that can be used to implement the technology disclosed. The computer system 1000 includes at least one central processing unit (CPU) 1072 that communicates with a number of peripheral devices via bus subsystem 1055. These peripheral devices can include a storage subsystem 1010 including, for example, memory devices and a file storage subsystem 1036, user interface input devices 1038, user interface output devices 1076, and a network interface subsystem 1074. The input and output devices allow user interaction with the computer system 1000. The network interface subsystem 1074 provides an interface to outside networks, including an interface to corresponding interface devices in other computer systems.

In one implementation, the identification engine 130 is communicably linked to the storage subsystem 1010 and the user interface input devices 1038.

User interface input devices 1038 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into the computer system 1000.

User interface output devices 1076 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from the computer system 1000 to the user or to another machine or computer system.

The storage subsystem 1010 stores programming and data constructs that provide the functionality of some or all of the modules and methods described herein. Subsystem 1078 can be graphics processing units (GPUs) or field-programmable gate arrays (FPGAs).

The memory subsystem 1022 used in the storage subsystem 1010 can include a number of memories including a main random access memory (RAM) 1032 for storage of instructions and data during program execution and a read only memory (ROM) 1034 in which fixed instructions are stored. A file storage subsystem 1036 can provide persistent storage for program and data files, and can include a hard disk drive, a floppy disk drive along with associated removable media, a CD-ROM drive, an optical drive, or removable media cartridges. The modules implementing the functionality of certain implementations can be stored by the file storage subsystem 1056 in the storage subsystem 1010, or in other machines accessible by the processor.

The Bus subsystem 1055 provides a mechanism for letting the various components and subsystems of the computer system 1000 communicate with each other as intended. Although the bus subsystem 1055 is shown schematically as a single bus, alternative implementations of the bus subsystem can use multiple busses.

The computer system 1000 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of the computer system 1000 depicted in FIG. 10 is intended only as a specific example for the purposes of illustrating the preferred embodiments of the present invention. Many other configurations of the computer system 1000 are possible having more or less components than the computer system depicted in FIG. 10.

The computer system 1000 includes GPUs or FPGAs 1078. It can also include machine learning processors hosted by machine learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligence Processing Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

We claim as follows:

1. A computer-implemented method of generating a scannable code for an authenticated user, the method including:
   securely sending, to a registration server, a unique identifier for the authenticated user, a cryptographic signature generated based at least in part upon a biometric identifier for the authenticated user, and a timestamp;
   receiving, from the registration server, a success nonce, usable by the registration server to access a user photo identifier and access a hash of at least the signature;
   recreating the hash of the at least the signature stored by the registration server;
   generating the scannable code including encrypting the success nonce and the recreated hash and producing the scannable code from results of the encrypting; and
   displaying the scannable code for a validator to scan for verifying that a return-to-work request is from the authenticated user;
   wherein the biometric identifier of the authenticated user was generated by feeding a plurality of non-deterministic biometric inputs, including a plurality of face images and a plurality of voice samples of a user, to a trained machine learning model producing a plurality of feature vectors, projecting the plurality of feature vectors onto a surface of a unit hyper-sphere and computing a characteristic identity vector representing the user based on the feature vectors as projected.

2. The method of claim 1, further including:
   receiving a shared encryption key and a public encryption key.

3. The method of claim 2, wherein the cryptographic signature for the authenticated user is generated by applying the shared encryption key to a biometric identifier for the authenticated user.

4. The method of claim 3, further including:
   sending to the registration server, for validating, signature for the unique identifier for the authenticated user.

5. The method of claim 3, further including:
   generating the hash of at least the signature and the shared key.

6. The method of claim 2, further including:
   encrypting the success nonce and the recreated hash with the public encryption key of the registration server.

7. The method of claim 1, further including:
   sending to the registration server, for validating, the timestamp, then generating the success nonce and the hash of at least the signature, then storing the nonce, the hash and the photo ID for the authenticated user.

8. The method of claim 1, recreating the hash further including:
   a shared key stored by the registration server.

9. The method of claim 1, wherein the success nonce is a one-time use code for use with the scannable code.

10. A computer-implemented method of verifying a return-to-work request from an authenticated user by a registration server, the method including:
    securely receiving, from a validator that has scanned a scannable code that encodes a nonce code, previously generated by the registration server, and a recreated hash, previously associated by the registration server with the nonce;
    extracting the nonce code and the recreated hash from the scannable code;
    using the nonce code to access a hash of record and photo ID of the authenticated user;

validating the recreated hash against a hash of record;
marking the nonce code as used; and
sending the validator, a photo of the authenticated user and a success message to return-to-work;
wherein the nonce code was previously generated by feeding a plurality of non-deterministic biometric inputs, including a plurality of face images and a plurality of voice samples of a user, to a trained machine learning model producing a plurality of feature vectors, projecting the plurality of feature vectors onto a surface of a unit hyper-sphere and computing a characteristic identity vector representing the user based on the feature vectors as projected.

11. The method of claim 10, wherein the recreated hash is generated using at least the signature for the authenticated user.

12. The method of claim 10, further including:
decrypting the success code with a private key of the registration server.

13. A non-transitory computer readable storage medium embedded with computer program instructions to generate a scannable code for an authenticated user, the instructions, when executed on a processor, implement a method comprising:
securely sending, to a registration server, a unique identifier for the authenticated user, a cryptographic signature generated based at least in part upon a biometric identifier for the authenticated user, and a timestamp;
receiving, from the registration server, a success nonce, usable by the registration server to access a user photo identifier and access a hash of at least the signature;
recreating the hash of the at least the signature stored by the registration server;
generating a scannable code including encrypting the success nonce and the recreated hash and producing the scannable code from results of the encrypting; and
displaying the scannable code for a validator to scan for verifying that a return-to-work request is from the authenticated user;
wherein the biometric identifier of the authenticated user was generated by feeding a plurality of non-deterministic biometric inputs, including a plurality of face images and a plurality of voice samples of a user, to a trained machine learning model producing a plurality of feature vectors, projecting the plurality of feature vectors onto a surface of a unit hyper-sphere and computing a characteristic identity vector representing the user based on the feature vectors as projected.

14. The non-transitory computer readable storage medium of claim 13, implementing the method further comprising:
receiving a shared encryption key and a public encryption key.

15. The non-transitory computer readable storage medium of claim 14, wherein the cryptographic signature for the authenticated user is generated by applying the shared encryption key to a biometric identifier for the authenticated user.

16. The non-transitory computer readable storage medium of claim 15, implementing the method further comprising:
sending to the registration server, for validating, signature for the unique identifier for the authenticated user.

17. The non-transitory computer readable storage medium of claim 15, implementing the method further comprising:
generating the hash of at least the signature and the shared key.

18. The non-transitory computer readable storage medium of claim 13, implementing the method further comprising:
sending to the registration server, for validating, the timestamp, then generating a success nonce and a hash of at least the signature, then storing the nonce, the hash and a photo ID for the authenticated user.

* * * * *